(12) United States Patent
Hoerig et al.

(10) Patent No.: US 12,036,073 B2
(45) Date of Patent: Jul. 16, 2024

(54) DATA-DRIVEN ELASTICITY IMAGING

(71) Applicant: The Board of Trustees of the University of Illinois, Urbana, IL (US)

(72) Inventors: Cameron Lee Hoerig, Champaign, IL (US); Michael F Insana, Urbana, IL (US); Jamshid Ghaboussi, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 834 days.

(21) Appl. No.: 16/812,023

(22) Filed: Mar. 6, 2020

(65) Prior Publication Data

US 2020/0281568 A1   Sep. 10, 2020

Related U.S. Application Data

(60) Provisional application No. 62/814,525, filed on Mar. 6, 2019.

(51) Int. Cl.
| | |
|---|---|
| *A61B 8/08* | (2006.01) |
| *A61B 5/00* | (2006.01) |
| *A61B 5/11* | (2006.01) |
| *G06N 3/045* | (2023.01) |
| *G16H 30/20* | (2018.01) |
| *G16H 50/20* | (2018.01) |
| *G16H 50/30* | (2018.01) |

(52) U.S. Cl.
CPC ............ *A61B 8/485* (2013.01); *A61B 5/1121* (2013.01); *A61B 5/7264* (2013.01); *A61B 5/7267* (2013.01); *A61B 8/5207* (2013.01); *A61B 8/5215* (2013.01); *G06N 3/045* (2023.01); *G16H 30/20* (2018.01); *G16H 50/20* (2018.01); *G16H 50/30* (2018.01)

(58) Field of Classification Search
CPC ..... A61B 8/485; A61B 8/5207; A61B 8/5215; A61B 5/7264; A61B 5/7267; G06N 3/045
See application file for complete search history.

(56) References Cited

U.S. PATENT DOCUMENTS

2017/0281094 A1* 10/2017 Ghaboussi ............ A61B 8/485

* cited by examiner

*Primary Examiner* — Amelie R Davis
(74) *Attorney, Agent, or Firm* — FisherBroyles, LLP; Richard M Lehrer; T. J. Dovale

(57) ABSTRACT

Systems and methods are provided for employing informational models trained using the Autoprogressive Algorithm to learn the mechanical behavior and internal structure of biological materials using a sparse sampling of force and displacement measurements. Forces are applied to the biological material and the force and displacement are measured and applied to the AutoP algorithm. Additionally, a coordinate based scaling factor is applied to the measured displacement.

20 Claims, 34 Drawing Sheets

(a)

(b)

(a)  (b)  (c)

DATA-DRIVEN ELASTICITY IMAGING

CROSS REFERENCE TO RELATED APPLICATIONS

This application claims the benefit of the filing date of U.S. provisional patent application No. 62/814,525, entitled "Data-Driven Elasticity Imaging", which was filed on Mar. 6, 2019, by the same patentee of this application and which shares the same inventor(s) as this application. That provisional application is hereby incorporated by reference as if fully set forth herein.

STATEMENT REGARDING FEDERALLY SPONSORED RESEARCH OR DEVELOPMENT

This invention was made with government support under R13 EB025662 and R01 CA 168575 awarded by the National Institutes of Health. The government has certain rights in the invention.

FIELD OF THE TECHNOLOGY

The technology/of this disclosure relates generally to mechanical property imaging of biological media, and more specifically but not exclusively to employing informational models to predict full stress and strain distributions from applied forces and learning the internal structure of the biological media from the stress and strain distributions by employing the Autoprogressive Algorithm that uses a Cartesian neural network constitutive model.

BACKGROUND OF THE INVENTION

Medical elasticity imaging maps biomechanical properties of soft tissues to aid in the detection and diagnosis of pathological states. Estimating mechanical properties from measurement data constitutes the inverse problem in elastography. A goal for quasi-static elastography is: given a set of force-displacement estimates and overall object shape, reconstruct the spatial distribution of mechanical properties.

Conventional quasi-static elasticity imaging techniques rely on model-based (or knowledge-driven) mathematical inverse methods to estimate mechanical parameters from force-displacement measurements. The mechanical properties of tissues are defined by parameters of a constitutive model relating stresses and strains. However, the data necessary to solve for material properties cannot normally be acquired due to measurement noise and limited force-displacement sampling from which stress-strain behavior is determined. Instead assumptions are imposed by selecting, for example, a plane-strain linear-elastic constitutive model that constrains the problem to closely match the data that can be acquired. Some strain information can be computed as spatial derivatives of the displacements, but stresses cannot be calculated from force data without knowing the object geometry, boundary conditions, and material properties.

Simplifying assumptions are adopted in conventional model-based techniques to help overcome the ill-posed nature of the inverse problem. Most often the tissue is assumed to be linear-elastic, isotropic, (nearly) incompressible, and under small strain, limiting the parameter space to only the Young's modulus (or shear modulus). However, biological tissues are bi-phasic media exhibiting nonlinear and viscoelastic properties not summarized by a single linear parameter.

While a chosen model may be appropriate for certain tissue types, it may be incorrect for other tissues in the same field of view. The constitutive model sets the parameters to be estimated and if an inappropriate model is chosen, parametric errors are made, corrupting the final elastogram. Further, the most diagnostic model parameters for each disease state have yet to be determined.

It may be advantageous to provide systems and methods for elasticity imaging of biological tissue which do not require constitutive model assumptions or prior knowledge of the internal structure of the biological media. It may be advantageous to provide systems and methods for elasticity imaging of biological tissue which simultaneously learn material property and geometric information independent of the internal structure of the tissue.

Brief Summary of the Technology

Many advantages will be determined and are attained by the technology of the present disclosure, which in a broad sense provides systems and methods for elasticity imaging of biological tissue using informational models to predict stress and strain distributions from applied forces without being required to engage specific constitutive models and without requiring prior knowledge of an internal structure of the tissue.

One or more embodiments of the technology provides a computer-implemented method for estimating stress and strain distributions in biological tissue without requiring estimations of underlying constitutive models or prior knowledge of the structure of the biological tissue. The method includes applying with a probe, a series of forces to the tissue. The method also includes recording, over a period of time, a series of displacement measurements respectively resulting from the forces, such that the measurements are recorded from multiple locations on the tissue. The method includes providing the force and displacement measurements to a processor-based device, and using the processor-based device to generate, based at least in part on the force and displacement measurements, the estimates of stress and strain distributions in the tissue. The method also includes learning spatial information by multiplying a strain vector by a stiffness matrix and computing a corresponding stress for various x,y coordinates. The method may include learning spatial information by multiplying a strain vector by a spatially varying value and computing a corresponding stress for various (x,y) coordinates.

One or more embodiments of the technology provides a system for characterization of mechanical properties of biological tissue and geometric information about the biological tissue. The system may include a force producing device, a measuring device configured to measure external force applied to the biological tissue and a processor in electrical communication with the measuring device. The processor may be programmed to measure a set of internal displacements from the tissue and to develop an informational model of mechanical properties of the tissue using the Autoprogressive algorithm. The processor may also be programmed to alter the informational model of mechanical properties based at least in part on a spatial coordinate input.

The technology will next be described in connection with certain illustrated embodiments and practices. However, it will be clear to those skilled in the art that various modifications, additions and subtractions can be made without departing from the spirit or scope of the claims.

BRIEF DESCRIPTION OF THE DRAWINGS

For a better understanding of the technology, reference is made to the following description, taken in conjunction with the accompanying drawings, in which like reference characters refer to like parts throughout, and in which.

Figure 1:
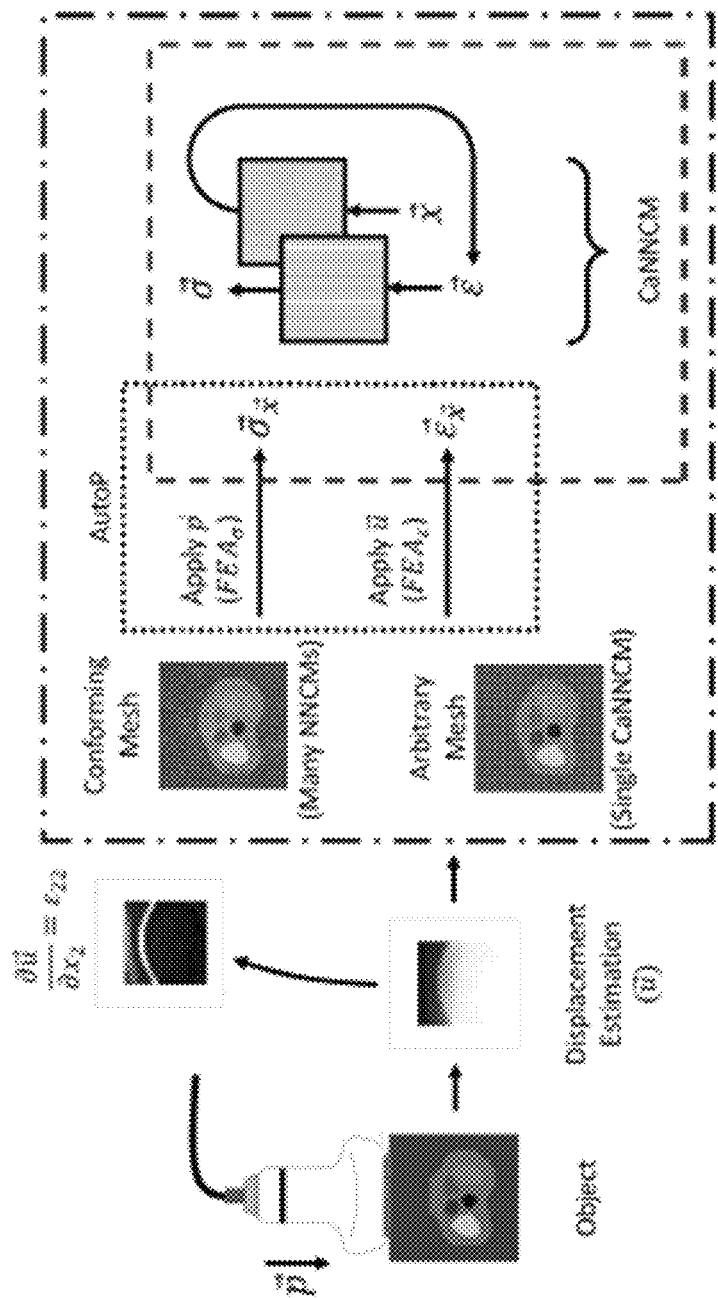
FIG. 1 illustrates an exemplary configuration of a system for performing elasticity imaging of biological tissue in accordance with one or more aspects of the described technology.

The technology will next be described in connection with certain illustrated embodiments and practices. However, it will be clear to those skilled in the art that various modifications, additions, and subtractions can be made without departing from the spirit or scope of the claims.

DETAILED DESCRIPTION OF THE TECHNOLOGY

Referring to the figures in detail, there is illustrated systems and methods for medical elasticity imaging in biological tissue using informational models to learn material property and geometric information about the tissue from force-displacement data. Estimating mechanical properties from measurement data constitutes the inverse problem in elastography. A goal for quasi-static elastography can be stated simply: given a set of force-displacement estimates and overall object shape, reconstruct the spatial distribution of mechanical properties. Time-varying force-displacement measurements are governed by the geometric and mechanical properties of the tissue and may provide diagnostic data relevant to cancer detection in the breast, liver and prostate, identifying atherosclerotic plaques, or treatment monitoring during high-intensity focused ultrasound or RF ablation.

The following description is provided as an enabling teaching as it is best, currently known. To this end, those skilled in the relevant art will recognize and appreciate that many changes can be made to the various aspects described herein, while still obtaining the beneficial results of the technology disclosed. It will also be apparent that some of the desired benefits can be obtained by selecting some of the features while not utilizing others. Accordingly, those with ordinary skill in the art will recognize that many modifications and adaptations are possible, and may even be desirable in certain circumstances, and are a part of the technology described. Thus, the following description is provided as illustrative of the principles of the technology and not in limitation thereof. Discussion of an embodiment, one or more embodiments, an aspect, one or more aspects, a feature or one or more features is intended be inclusive of both the singular and the plural depending upon which provides the broadest scope without running afoul of the existing art and any such statement is in no way intended to be otherwise limiting in nature. Technology described in relation to one of these terms is not necessarily limited to use in that embodiment, aspect or feature and may be employed with other embodiments, aspects and/or features where appropriate.

The following description provides an approach to elasticity imaging of biological media that does not require assumptions about tissue mechanical properties, including linearity and isotropy, although it does not necessarily restrict the use either. It also does not require prior knowledge of the internal structure of the tissue.

The initial focus is on quasi-static methods that generate full stress and strain maps from force-displacement measurements and knowledge of external object shape. The stress and strain maps are used to learn the internal structure of the biological media. This is done using Cartesian neural network constitutive models (CaNNCMs) which can use data to model both linear-elastic mechanical properties and their distribution in space. Furthermore, a trained CaNNCM can be used to reconstruct a Young's modulus image.

Elasticity images map biomechanical properties of soft tissues to aid in the detection and diagnosis of pathological states. In particular, quasi-static ultrasonic (US) elastography techniques use force-displacement measurements acquired during an US scan to parameterize the spatio-temporal stress-strain behavior. A data-driven method for building neural network constitutive models (NNCMs) that learn stress-strain relationships from force-displacement data was previously described in co-pending U.S. patent application Ser. No. 15/480,270 entitled "Information Based Machine Learning Approach to Elasticity Imaging" (the "co-pending application") which is incorporated herein by reference as if fully set forth.

The present disclosure introduces Cartesian neural network constitutive models (CaNNCMs) that are capable of using data to model both linear-elastic mechanical properties and their distribution in space. CaNNCMs can capture arbitrary material property distributions using stress-strain data from simulated phantoms. A trained CaNNCM can be used to reconstruct a Young's modulus image. CaNNCMs are an important step toward data-driven modeling and imaging the complex mechanical properties of soft tissues.

Elasticity imaging methods reconstruct a map of mechanical properties by observing tissue motion in response to a weak mechanical stimulus. For quasi-static ultrasonic elastography, measurement data are forces and displacements as an ultrasound (US) probe is slowly pressed into the tissue surface. As discussed in the co-pending application, the technology is not limited to US probes. Recorded displacements may include both probe motion and internal tissue deformation, the latter being estimated via speckle-tracking algorithms operating on pre- and post-deformation echo data. These time-varying force-displacement measurements are governed by the geometric and mechanical properties of the tissue and may provide diagnostic data relevant to cancer detection in the breast, liver, and prostate, identifying atherosclerotic plaques, or treatment monitoring during high-intensity focused ultrasound or RF ablation.

Estimating mechanical properties from measurement data constitutes the inverse problem in elastography. A goal for quasi-static elastography can be stated simply: given a set of force-displacement estimates and overall object shape, reconstruct the spatial distribution of mechanical properties. The technology may implement a data-driven approach using artificial neural networks ("NNs" or "ANNs") in place of a pre-defined constitutive model. These NN constitutive models (NNCMs) learn stress-strain behavior from force-displacement measurements without any initial assumptions of mechanical behavior. After training, NNCMs can be used to compute all relevant stresses and strains, from which material parameters from any constitutive model can be estimated. A block diagram of a method is shown in FIG. 1. After acquiring force-displacement measurements, a finite element (FE) mesh is created that conforms to both the internal and external geometries of the object from prior knowledge or manual segmentation of the US images. The mesh and measurement data are used in the Autoprogressive Algorithm (AutoP) to train NNCMs for each region exhibiting unique material properties.

This method may train NNCMs to accurately characterize the linear-elastic properties of gelatin phantoms in 2-D and 3-D and obtain Young's modulus estimates of rabbit kidneys. However, prior knowledge of object geometry may not be available in a clinical setting, nor can it be assumed that tissue boundaries observed in an US image always correspond to actual material property boundaries. A utility of NNCMs and AutoP for elastography may be enhanced by altering the network architecture to incorporate learning of spatial information.

Cartesian neural network constitutive models (CaNNCMs) address this issue. CaNNCMs accept Cartesian coordinate information as additional inputs to simultaneously learn material property and geometric information independent of the internal structure represented by the FE mesh. This CaNNCM architecture learns spatial distributions of material properties from stresses and strains. The following examples use stress-strain data acquired from simulated phantoms to demonstrate the ability of CaNNCMs to model material property distributions on an arbitrary FE mesh without affecting the learned mechanical behavior. Because CaNNCMs capture spatial information, an elastogram may be reconstructed directly from a trained model.

Further, in the presence of noise or changes to the FE mesh, CaNNCMs remain able to accurately model linear-elastic mechanical behavior.

AutoP has been primarily developed and used in civil and geotechnical engineering applications to model the mechanical properties of various materials and structures. The AutoP approach to constitutive modeling is to apply force-displacement measurements to two finite element analyses ("FEAs") associated with a mesh of an imaged object. Forces and displacements applied in separate finite element analyses are connected through NNCMs. NNCMs can be trained to consistently relate measured forces and displacements, such that application of measured forces in a FEA results in the measured displacements and vice-versa.

Ultrasonic imaging provides internal displacement estimates which may be imposed in AutoP along with surface displacements. The extra displacement data may be used to develop NNCMs that learn the linear-elastic behavior of gelatin phantoms; however, because the FE mesh matched both the internal and external phantom geometry, only a sparse sampling of the internal data was necessary.

Internal displacements under a quasi-static load provide an enormous amount of information regarding internal structure. Because the force stimulus has time to propagate throughout the entire object before force-displacement measurements are acquired, displacements at one location are affected by deformation at all other points in the object. Previously, the NNCMs ignored the spatial aspects of measurements when relating stress to strain. The new NNCM architecture may incorporate spatial information to make it possible to relax the geometric constraints on the FE mesh. Cartesian NNCMs are capable of learning both material and internal geometric properties for the task of forming elasticity images.

The NN structure may be designed to represent the input/output relationship and the intermediate computations that must be performed. In the co-pending application, a simple feed-forward, fully connected architecture was sufficient (left side of FIG. 2A). NNCMs computed a stress vector output from a strain vector input. The possible positive and negative input/output values were accounted for—and the sign symmetry between stresses and strains—by using hyperbolic tangent activation functions. The choice of hyperbolic tangent ensures that under zero strain, there is zero stress. To avoid saturating the input nodes and keep the NNCMs sensitive to changes in the input strains, a scaling vector $S^\varepsilon$ was selected to scale each component of the input strains within the ±0.8 range. Similarly, the output is bounded to ±1.0 whereas stresses can extend well beyond that range. As such, a different scaling vector $S^\sigma$ was selected to keep the output within ±0.8. The flow of data through the NNCM was therefore $\varepsilon \rightarrow \varepsilon/S^\varepsilon \rightarrow NNCM \rightarrow \sigma/S^\sigma \rightarrow \sigma$, where the vector divisions are element-by-element operations. This type of NNCM is referred to as a material property network (MPN) 100.

Figure 2A:
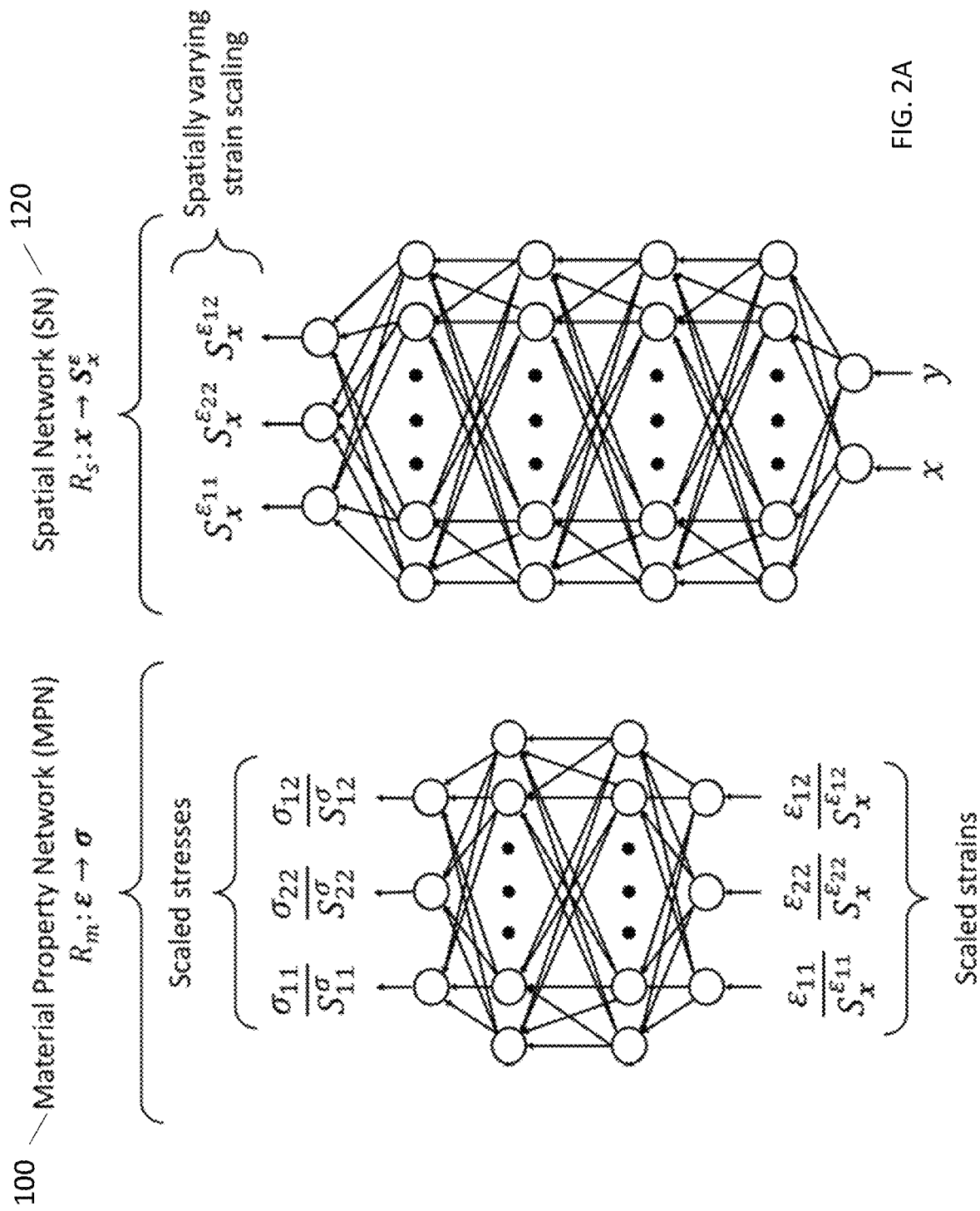
FIG. 2A illustrates a Cartesian Neural Network Constitutive Model for use with the system of FIG. 1 in accordance with one or more aspects of the described technology.
Figure 2B:
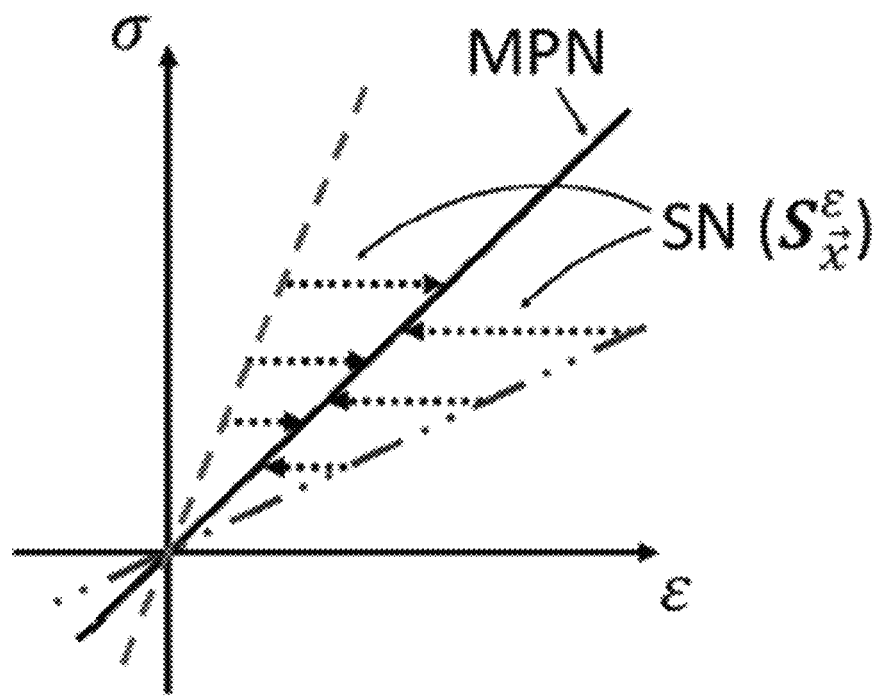
FIG. 2B illustrates an interaction between an MPN and SN in accordance with one or more aspects of the described technology.

As illustrated in FIG. 2A, to create a NNCM to learn internal structure, spatial information was added in the flow of data through the network. Instead of increasing the number of inputs to include spatial coordinates, scaling factors are learned to alter the material properties characterized by the MPN. Consider the stress-strain behavior represented by the MPN with $S^\varepsilon_x=1$ to be the "reference" material property (i.e., $R_m: \varepsilon \rightarrow \sigma$). FIG. 2B illustrates that for the case of linear-elastic materials, the stress-strain diagram is a straight line with a slope that is the Young's modulus as determined by the MPN. Stresses are computed by simply multiplying a strain vector by the stiffness matrix C: $\sigma=C\varepsilon$.

Changing the strain scaling at a point (x, y) alters the slope of the line, effectively changing the Young's modulus at that location. CaNNCMs may accomplish this change by introducing a spatial network (SN) that computes $S^\varepsilon_x$ based on a coordinate input (right side of FIG. 2A). A SN is the function $R_s$: $x \rightarrow S^\varepsilon_x$. The stress scaling vector may also be reduced to a single value: $S_{11}^\sigma = S_{22}^\sigma = S_{12}^\sigma = S^\sigma$.

The spatial scaling values produce a map of relative stiffnesses where larger $S^\varepsilon_x$ tend to correspond to softer regions. To understand why, consider the reference linear-elastic relationship learned by the MPN. Under uniaxial loading, a heterogeneous material exhibits large strains and small stresses in soft regions. In contrast, stiff regions produce large stresses for small strains. Therefore, larger $S^\varepsilon_x$ values in soft regions decrease the magnitude of the strain vector input to the MPN. Similarly, smaller scaling values in stiff regions result in larger strains after scaling. In broad terms, $S^\varepsilon_x$ acts as a function transformation for the relationship learned by the MPN: $\sigma/S^\sigma_x = f(\varepsilon/S^\varepsilon_x)$. In the more specific case of linear-elastic materials, the SN acts as a spatially-varying matrix that operates on the strains before multiplying by the stiffness matrix: $\sigma = CE(x, y)\varepsilon$. The interaction between the MPN and SN is illustrated in FIG. 2B. Together, the networks learn the mapping Rm, Rs: $\varepsilon(x) \rightarrow \sigma(x)$.

The SN 120 may also have a fully connected, feed-forward architecture. Unlike the MPN counterpart, spatial networks use a mix of logistic and hyperbolic tangent activation functions. Considering that the output $S^\varepsilon_x$ is always positive, the logistic function is a natural choice for the output nodes. Conversely, the input (x, y) can span the positive and negative range, but a vector of zeros at the input does not imply the output should also be zero. Thus, a logistic activation function is employed for the first layer as well. All intermediate layers may use a hyperbolic tangent. As with the MPN, the spatial network inputs and outputs are bounded: input values outside the ±1.0 may saturate the input nodes (and reduce sensitivity) while outputs not contained within (0, 1) cannot be achieved by a logistic function. The input (x, y) values are thus scaled to within ±1.0. Preliminary tests showed that setting the coordinate origin to the center of the FE mesh produced the best results. A similar shifting and scaling to the 0.1-0.8 range is performed for the output $S^\varepsilon_x$ values before training the spatial network.

Both the material property 100 and scaling networks 120 may learn from the same set of stress-strain data. These data may be estimated in AutoP after applying force and displacement measurements in FEAs. Each network may extract different information from the same set of data. Splitting the material property and geometry problems allows each network to learn a simpler input-output relationship. Combining the two networks results in a cooperative CaNNCM structure that captures both mechanical behavior and its geometric variation.

Inputs to the SN—Cartesian coordinates x—are defined by the FE mesh and are thus known a priori. Given a trained MPN, spatially varying stresses $\sigma(x)$, strains $\varepsilon(x)$ and coordinates, the task of determining the target output of the SN remains. The MPN and SN are cooperative and therefore work together to minimize errors between the stress vector output from the MPN and the "target" stress. Gradient-descent methods may be utilized for computing $S^\varepsilon_x$ based on the difference between stress estimated by the MPN in response to a strain input and the target stress $\sigma^t$ computed via FEA. Similar to the backpropagation algorithm for updating ANN connection weights, the error at the output of the MPN can be propagated back to the spatial scaling values. For simplicity, consider the stress $\sigma^t(x)$ and strain $\varepsilon(x)$ computed by FEA at a single location x. The current value of $S^\varepsilon_x$ and $\varepsilon(x)$ can be used to compute $\sigma^{NN}(x)$, the value of stress predicted by the MPN: $R_m$: $\varepsilon(x) \rightarrow \sigma^{NN}(x)$. A goal may be to minimize the objective function $$S^\varepsilon_x = \underset{S^\varepsilon_x \in R}{\arg\min} f_m(\sigma^t(x), \sigma^{NN}(x)). \tag{1}$$

The function $f_m(\bullet)$ is the L2 norm:

$$f_m = E = \frac{1}{2}\sum_{i=1}^{3} (\sigma_i^t(x) - \sigma_i^{NN}(x))^2 \tag{2}$$

$$= \frac{1}{2}\sum_{i=1}^{3} \varepsilon_i^2, \tag{3}$$

where (dropping (x) for brevity)

$$\sigma_i^{NN} = S_\sigma \sigma_i'^{NN} \tag{4}$$

$$\varepsilon_j = S_{x_i}^{\varepsilon_j} \varepsilon_j' \tag{5}$$

$$\varepsilon_i = \sigma_i^t - \sigma_i^{NN}. \tag{6}$$

$\sigma_k^t$ may be defined as the kth component (there are three components in the stress vector for 2-D models, ordered as $[\sigma_{11}, \sigma_{22}, \sigma_{12}]$ and the same ordering is used for the strain vector) of "target" stress at $x_i$; $\sigma_k^{NN}$ is the corresponding stress component predicted by the MPN in response to $\varepsilon$, and (i, j, k) having the range (1, 2, 3). Scaled input and outputs of the MPN are denoted as $\varepsilon'_j$ and $\sigma'^{NN}$, respectively. Calculating the partial derivate of the error with respect to $S_{x_i}^{\varepsilon_k}$ is straightforward:

$$\frac{\partial E}{\partial S_x^{\varepsilon_k}} = \frac{\partial}{\partial S_x^{\varepsilon_k}} \frac{1}{2}\sum_{i=1}^{3} \varepsilon_i^2 \tag{7}$$

$$= \sum_{i=1}^{3} \varepsilon_i \left[\frac{\partial}{\partial S_x^{\varepsilon_k}}(\sigma_i^t - \sigma_i^{NN})\right].$$

The partial derivative is distributed to the stress terms, noting that $\sigma^t_i$, was computed in a FEA and the partial derivative with respect to $S_{x_i}^{\varepsilon_k}$ is zero. For $\sigma^{t,NN}$ the chain rule may be invoked:

$$= \sum_{i=1}^{3} \varepsilon_i \left[-\sum_{j=1}^{3} \frac{\partial \sigma_i^{NN}}{\partial \varepsilon_j} \frac{\partial \varepsilon_j}{\partial S_x^{\varepsilon_k}}\right]. \tag{8}$$

The term $\partial \sigma_i^{NN}/\partial \varepsilon_j = D_{ij}$ is the stiffness matrix relating stress to strain and can be calculated via the weights of the material property network. Computing the last factor in the braces:

$$\frac{\partial \varepsilon_j}{\partial S_x^{\varepsilon_k}} = \frac{\partial}{\partial S_x^{\varepsilon_k}}(S_x^{\varepsilon_k}\varepsilon'_j) \tag{9}$$

$$= \varepsilon'_j \delta_{kj},$$

Where $\delta_{kj}$ is the Kronecker delta function. The final expression for the error gradient may be:

$$\frac{\partial E}{\partial S_x^{\varepsilon_k}} = -\sum_{i=1}^{3} \varepsilon_i \sum_{j=1}^{3} D_{ij} e'_j \delta_{jk}. \quad (10)$$

The update increment for $S_x^{\varepsilon_k}$ is the negative of the gradient multiplied by the value $\eta$ to adjust the increment size:

$$\Delta S_x^{\varepsilon_k} = \eta \sum_{i=1}^{3} \varepsilon_i \sum_{j=k} D_{ij} e'_j. \quad (11)$$

In Eq. 11, the inner sum is approximately equal to the stress computed by the MPN with all j≠k components of the scaled input strain vector set to zero. This stress vector is referred to as $\hat{\sigma}^{\cdot,NN}{}_i$. While it is possible to calculate $D_{ij}$ directly, the computational load may be reduced with this approximation, leading to a final equation for $\Delta S_x^{\varepsilon_k}$:

$$\Delta S_x^{\varepsilon_k} \approx \eta \sum_{i=1}^{3} e_i \hat{\sigma}_i^{i,NN} \quad (12)$$

Computing $\Delta S_{x_i}^{\varepsilon_k}$ using Eq. 12 is not significantly different from Eq. 11 and is nearly two orders of magnitude faster. Controlling the increment size with $\eta$ is equivalent to applying learning rate in backpropagation. Equations 2-12 and Algorithm 1 are shown for 2-D but can be easily extended to 3-D (the stresses and strains have 6 components in 3-D as opposed to the 3 components in 2-D).

Eq. 1 attempts to minimize the stress error for a single stress-strain pair. However, many stress-strain pairs may exist at x. Thus, it may be preferable, but not required, to minimize the stress error in an average sense for all stress-strain pairs at x. This may be accomplished by invoking Eq. 12 for each data pair at x and computing the mean of $\Delta S_{x_i}^{\varepsilon}$ before adding to $S_x^{\varepsilon}$.

A single application of Eq. 12 may be insufficient for updating $S_x^{\varepsilon}$. Algorithm 1 details an iterative process for computing a new $S_x^{\varepsilon}$ at location x. N corresponds to the number of gradient-descent iterations and $N^{\sigma}$ is the number of stress-strain pairs at x.

| Algorithm 1 Iterations for computing $S_x^{\varepsilon}$ |
| --- |
| 1:     Given: current $S_x^{\varepsilon}$, $\sigma_i$, $\varepsilon_i$ at x |
| 2:     for n = 1, 2, ..., N do |
| 3:         for k = 1, 2, 3 do |
| 4:             $\Delta S = 0$ |
| 5:             for i = 1, 2, ..., $N^{\sigma}$ do |
| 6:                 Compute $\sigma_i^{NN}$ and (vector) $\hat{\sigma}_i^{\cdot,NN}$ using $\varepsilon_i$ |
| 7:                 Compute $e_i = \sigma_i^t - \sigma_i^{NN}$ |
| 8:                 Compute $\Delta S = \Delta S + \Sigma_{p=1}^{3} e_p \hat{\sigma}_p^{\cdot,NN}$ |
| 9:             end for |
| 10:           $\Delta S_x^{\varepsilon_k} = \eta \Delta S / N^{\sigma}$ |
| 11:           $S_x^{\varepsilon_k} = S_x^{\varepsilon_k} + \Delta S_x^{\varepsilon_k}$ |
| 12:        end for |
| 13:    end for |

Computing the stress scaling value $S^{\sigma}$ is far simpler. It may be chosen to ensure all components of every stress vector falls within the ±0.8 range. This follows from upper and lower bounds of the hyperbolic tangent activation function being ±1.0. In this example, setting $S^{\sigma}=1.0$ is sufficient because the magnitude of every computed stress falls below 0.8.

Figure 3A:
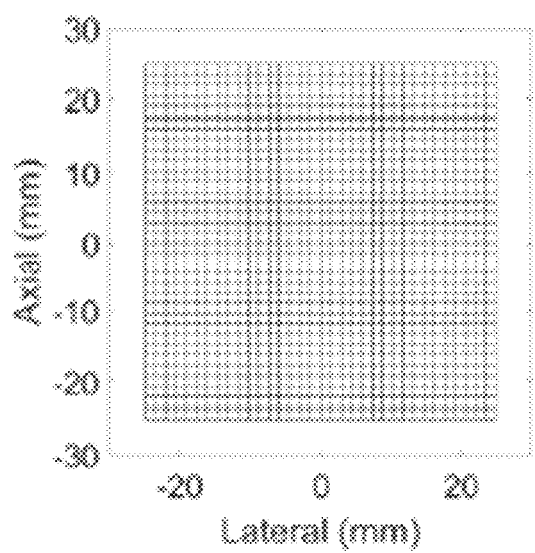
FIG. 3A illustrates a rectilinear mesh in accordance with one or more aspects of the described technology.

CaNNCMs were evaluated using simulated data under the ideal circumstance of stresses and strains being known exactly, and hence this study is confined to the dashed-line box in FIG. 1. Stress-strain data were generated by FEA (using ABAQUS 6.13) with known Young's modulus distributions. A simple four-node, quadrilateral element rectilinear mesh with 35 nodes per 50 mm edge (FIG. 3a) was selected to demonstrate the independence of CaNNCMs to the FE mesh. In the FEA, we used a plane-stress, incompressible (Poisson's ratio $\mu=0.5$) material model, the bottom surface of mesh was pinned to create a fixed boundary condition (BC), and a US probe was pressed into the top surface. The probe-phantom interface was modeled as frictionless to allow lateral motion of the top phantom surface during compression. Four equal compressive loads were applied by the probe up to 13.57 mN, leading to a minimum probe displacement of 0.98 mm and a maximum of 2.23 mm depending on the material property distribution.

Figure 4:
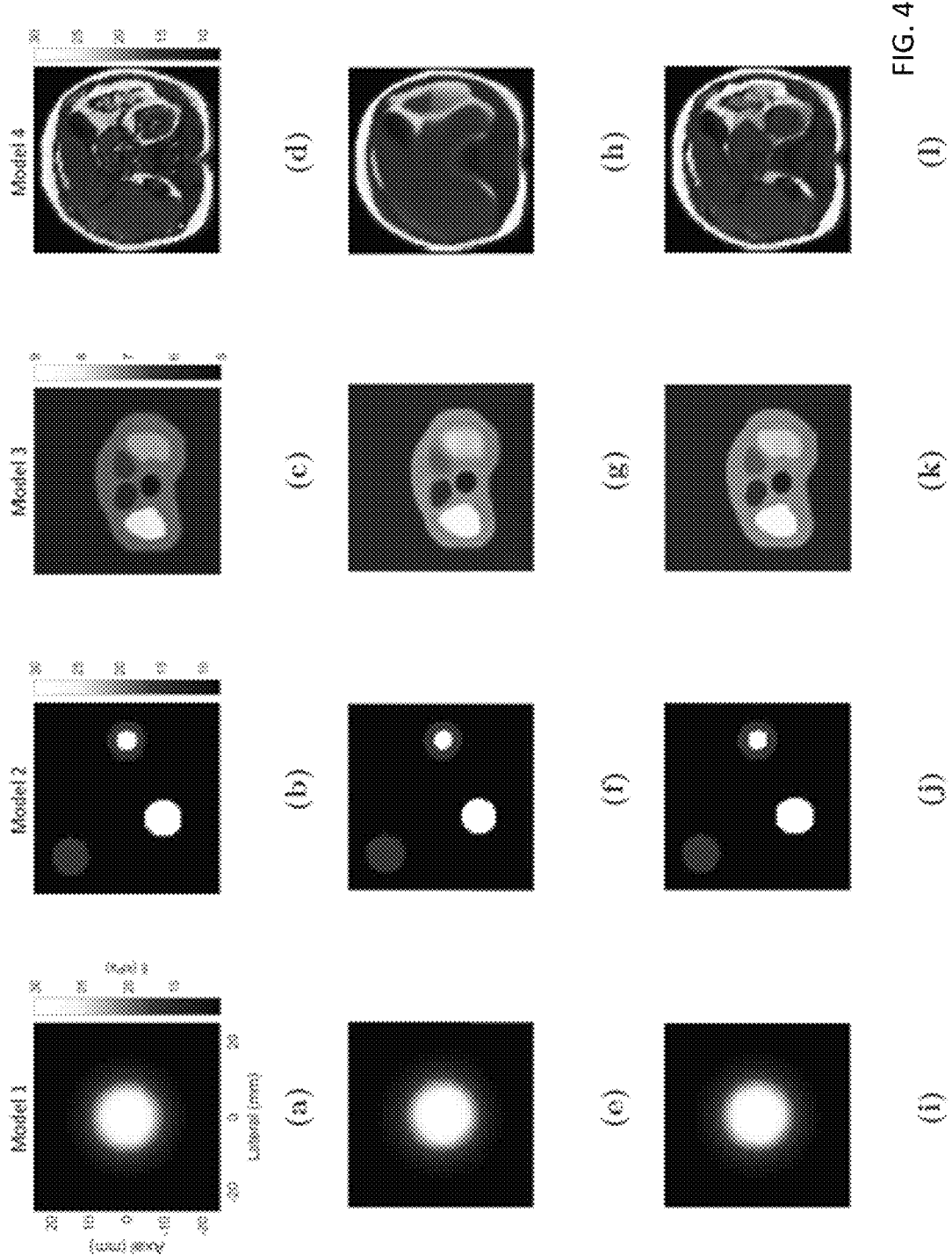
FIG. 4 illustrates Young's Modulus distributions in accordance with one or more aspects of the described technology.

Four different simulated phantom models, displayed in the top row of FIG. 4, were selected to test different aspects of CaNNCMs. Model 1 (FIG. 4a) is a stiff, Gaussian-shaped inclusion embedded in a soft background. The peak Young's modulus of the inclusion was 30 kPa and smoothly transitioned into the 10 kPa background. This model demonstrates the ability of CaNNCMs to capture smooth, continuous material property distributions. Models 2 and 3 have abrupt transitions in the material property distributions. Model 2 contains three stiff inclusions (15 kPa and 30 kPa) in an 8 kPa background. Model 3 represents a rabbit kidney embedded in a block of gelatin. Previously seven NNCMs were trained in AutoP with the force-displacement measurements. The Young's modulus values chosen for this simulated phantom correspond to the moduli estimated from those seven NNCMs. Model 4 was selected as an extreme case of complex spatial geometry. To generate this model, the gray-scale values of an abdominal MRI scan were scaled to the 8-30 kPa range of Young's modulus values. Model 4 does not represent a real case of elasticity imaging. The image was chosen for its geometric complexity while also representing human physiological structure.

Two additional data sets were generated with Model 3 after adding noise to the target Young's modulus distribution. Uniformly distributed random values up to ±10% and ±30% the local Young's modulus value (≈27.2 dB and ≈17.6 dB peak signal-to-noise ratio, respectively) were added to the target distribution of Model 3. Two different corrupted target distributions were generated for each test, performing the FEA with the loads and BCs previously specified, and compiled stresses from one analysis and strains from the other. Diagrams describing the data generation techniques are provided in FIGS. 8a and 8b.

Figure 3B:
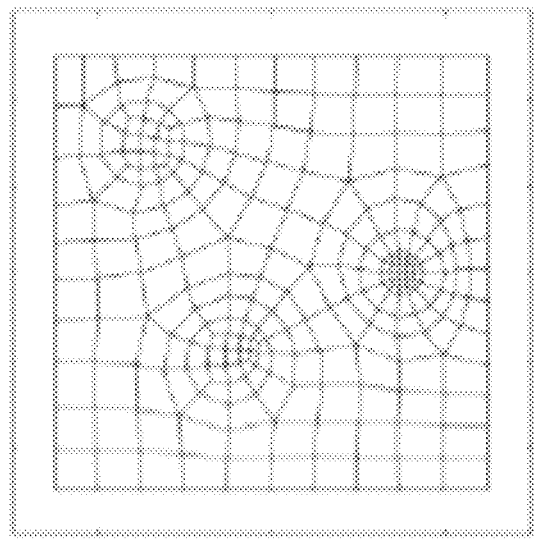
FIG. 3B illustrates a FE mesh in accordance with one or more aspects of the described technology.

Mesh 2 (FIG. 3b) conforms to the geometry of Model 2. The same force loads, and BCs described above were applied in a FEA of this model to generate the stress-strain data. While CaNNCMs are independent of the internal FE mesh structure, the learned distribution of stresses and strains may be affected. For example, the inner inclusion of Model 2 fills four elements in Mesh 1 and partially fills twelve adjacent elements. Conversely, 16 elements in Mesh 2 comprise the same nested inclusion. Furthermore, there are 1156 total elements in Mesh 1 and 235 in Mesh 2. The ratio of generated data from that one inclusion to all other points greatly increases and more accurately captures the geometry.

Before the spatial scaling values were computed for each model, a MPN was pretrained. A trained MPN may be used as a reference for updating $S_x^\varepsilon$. The material property network includes two hidden layers with six nodes per layer. Weights were initialized by drawing from a uniform distribution in the range [−0.2, 0.2]. 5000 strain vectors were generated, whose components were also randomly generated uniformly in the range [−0.2, 0.2], and computed the corresponding stress vectors using a plane-stress model with a Young's modulus value of 10 kPa and Poisson's ratio ν=0.5. Note that the initialization range for the weights and the strain vectors do not have to match. Previous results suggested this range performed well for the MPN. As for the strains, a range was chosen that extends beyond the magnitude of the strain vectors generated for the aforementioned models. Before weight update via the resilient backpropagation (RPROP) algorithm, frame invariance of the stresses and strains was enforced by rotating the frame of reference 90° and appending the new, rotated data to the original set, doubling the total number of training pairs. This rotation was done by simply swapping the axial and lateral components of the data and was implemented previously with AutoP. The MPN was trained over 50 epochs with $S_x^\varepsilon=1$ and $S^\sigma=1$.

After generating all data sets and pretraining the MPN, the stress-strain data from all four load increments was used in each set to compute new spatial scaling values using Alg. 1 (N=150, $N^\sigma$=8 due to frame invariance, η=2.5). Spatial networks were trained for each model using the newly computed $S_x^\varepsilon$. Each network included five hidden layers with 25 nodes per hidden layer. Training was split into iterations to mimic what occurs in AutoP. For example, instead of simply training the SN over 12000 epochs, training was split into iterations where fewer epochs were used. 10 iterations of 300 epochs were used in Test 1 whereas 30 iterations of 600 epochs were used in Test 2. These were equivalent to training for 3000 and 12000 epochs in a single iteration, respectively. Training for the SN was implemented in TensorFlow using He initialization of the weights, the Adam optimizer with default settings, and a learning rate of 0.03.

The trained spatial network for each model was then paired with the pretrained material property network to form a CaNNCM and used to reconstruct the Young's modulus image. Reconstruction using only a CaNNCM may be done by setting a constant strain vector ε=[0.003 0.005 0.0001] and varying (x, y) over the domain of the mesh. At each (x, y), a corresponding stress σ was computed. Axial and lateral components of the input strain vector ($\varepsilon_{11}$ and $\varepsilon_{22}$, respectively) and the axial component of the computed stress ($\sigma_{22}$) were used to compute the spatially varying Young's modulus E(x, y) by inverting the plane-stress equation:

$$E(x, y) = \frac{\sigma_{22}(1-\nu^2)}{\nu\varepsilon_{11} + \varepsilon_{22}} \quad (13)$$

where ν=0.5. The choice of strain vector is arbitrary so long as it resides within the range of training data. Selecting small values for each component ensured the strain was within the selected range.

Figure 5:
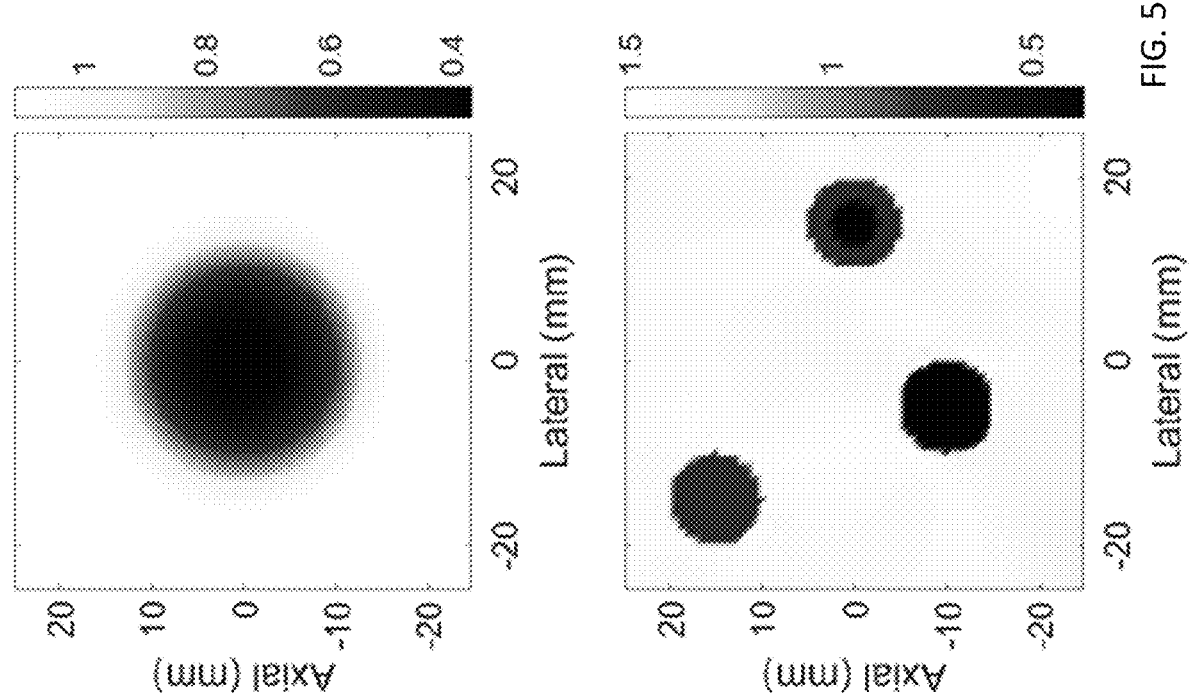
FIG. 5 illustrates results of computing spatial scaling values for seven study cases.
Figure 5:
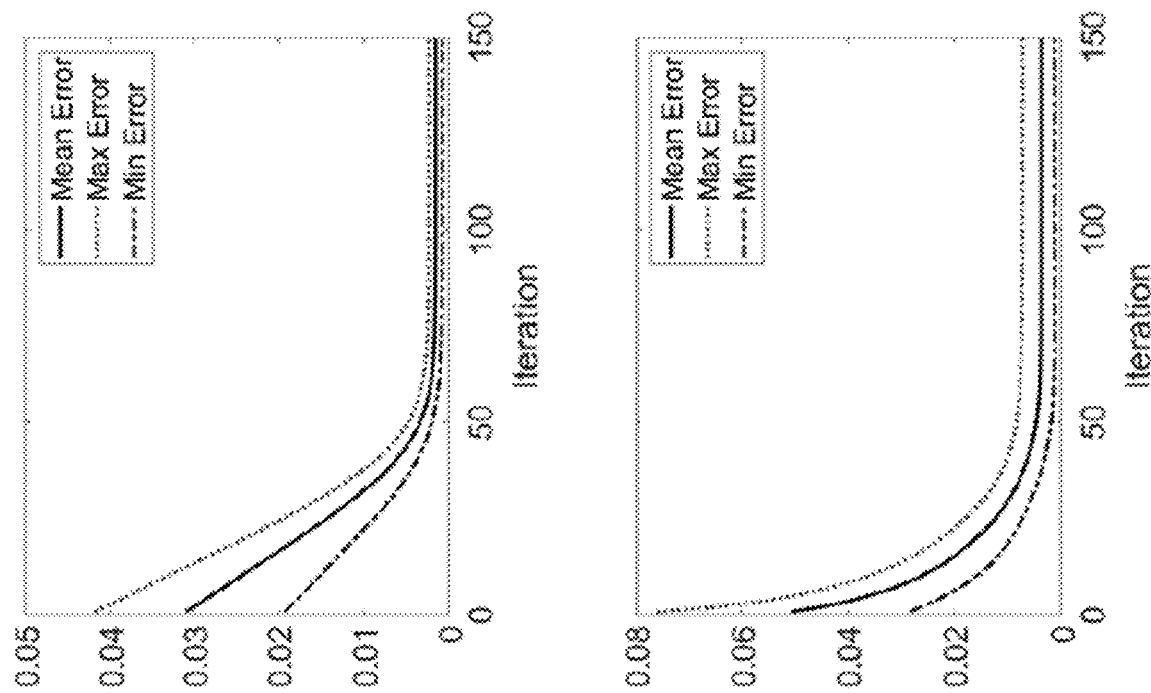
Figure 5:
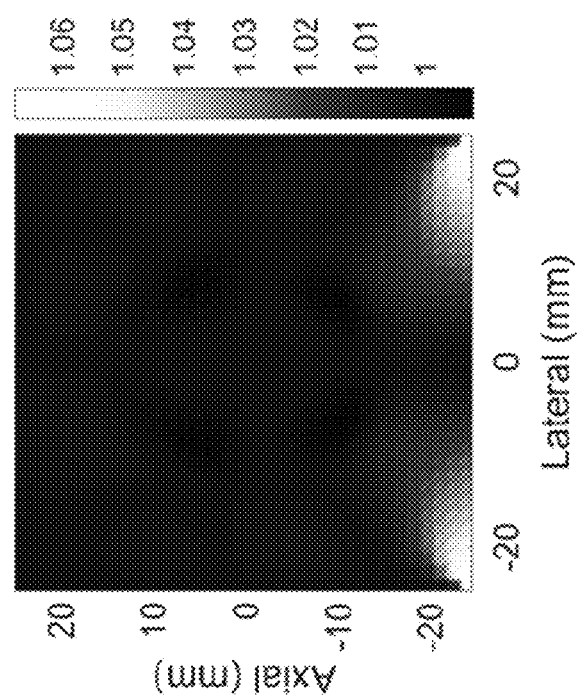
Figure 5:
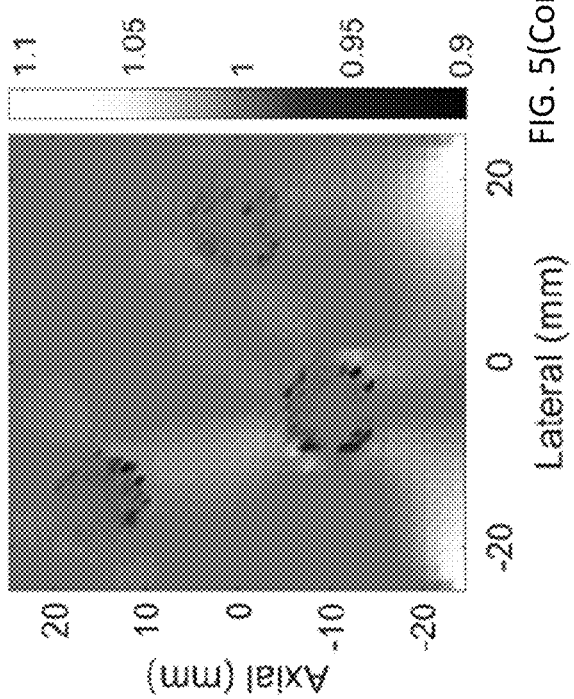
Figure 5:
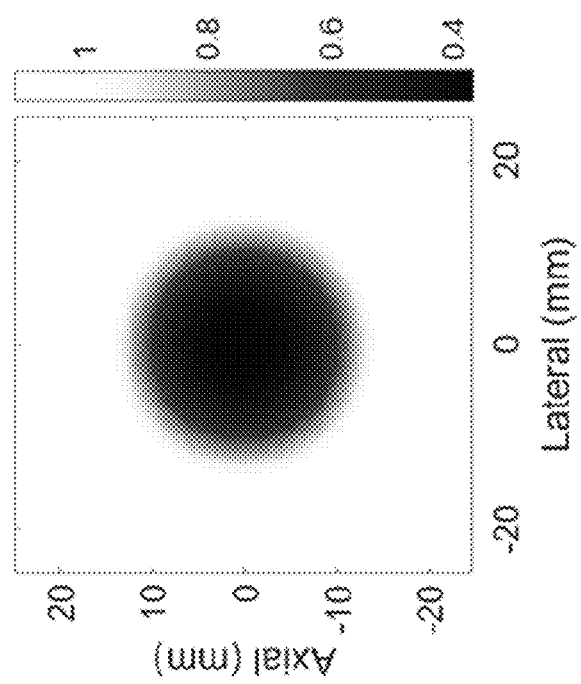
Figure 5:
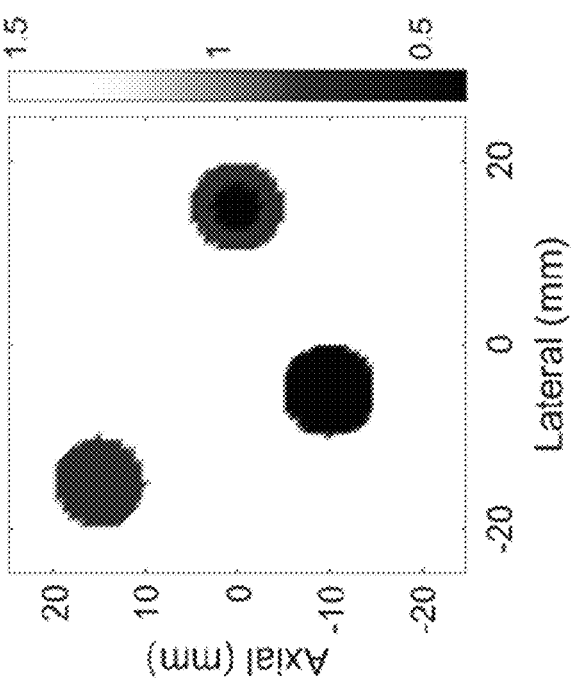
Figure 5:
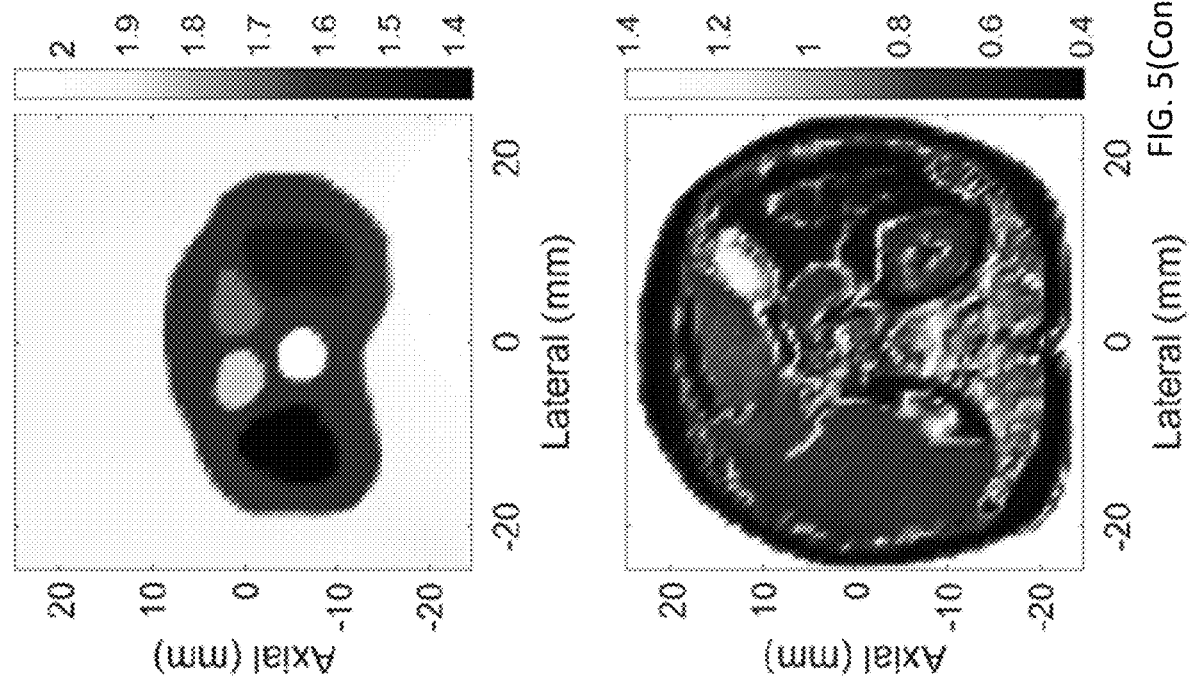
Figure 5:
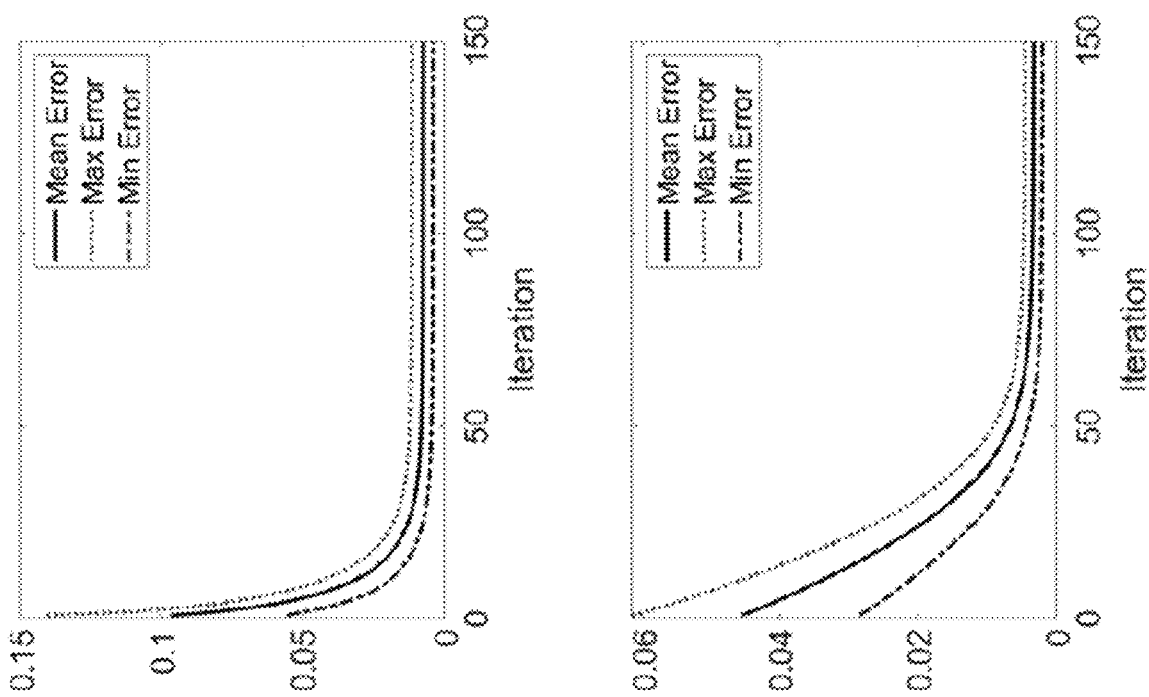
Figure 5:
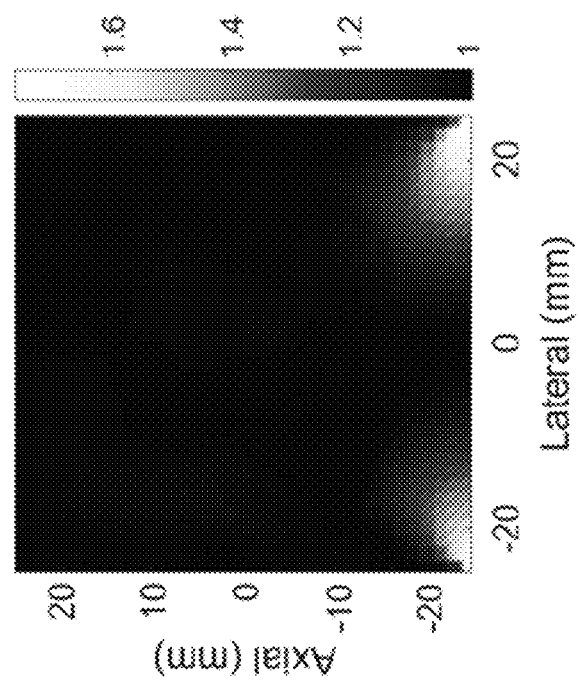
Figure 5:
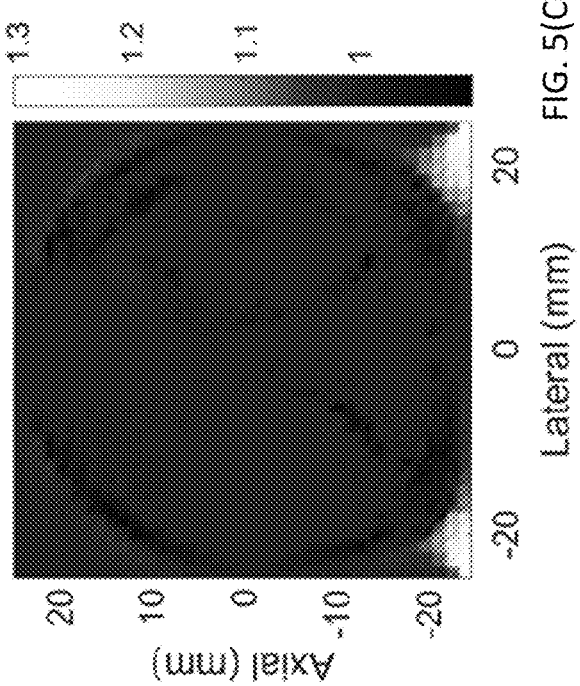
Figure 5:
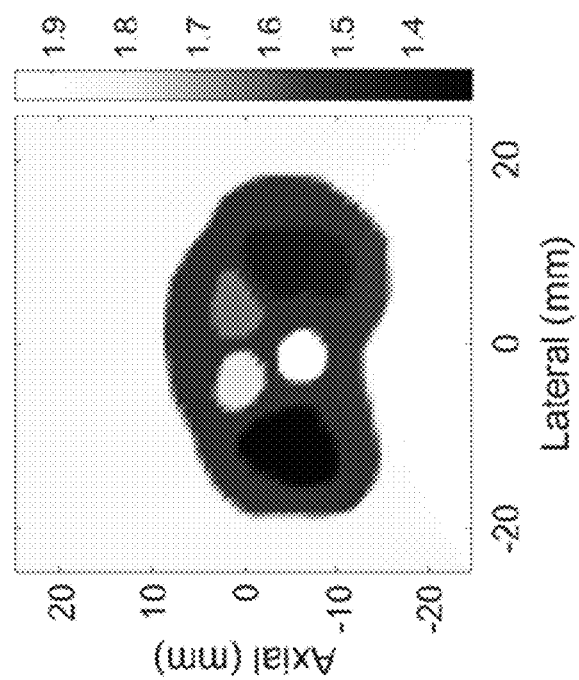
Figure 5:
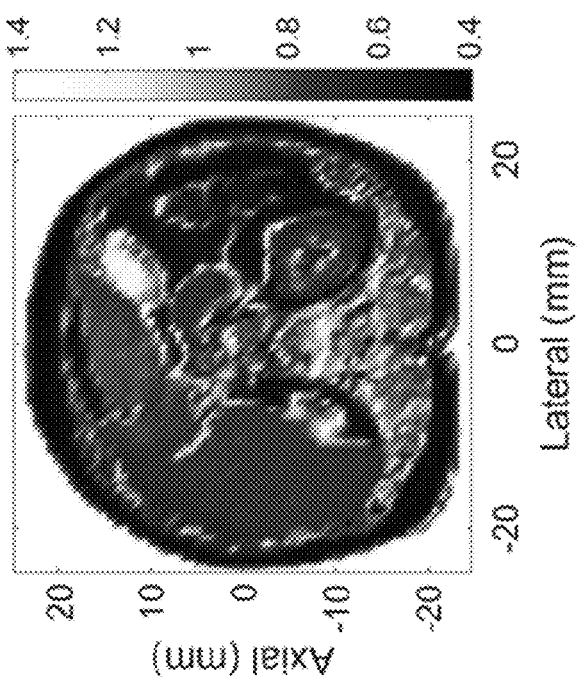
Figure 5:
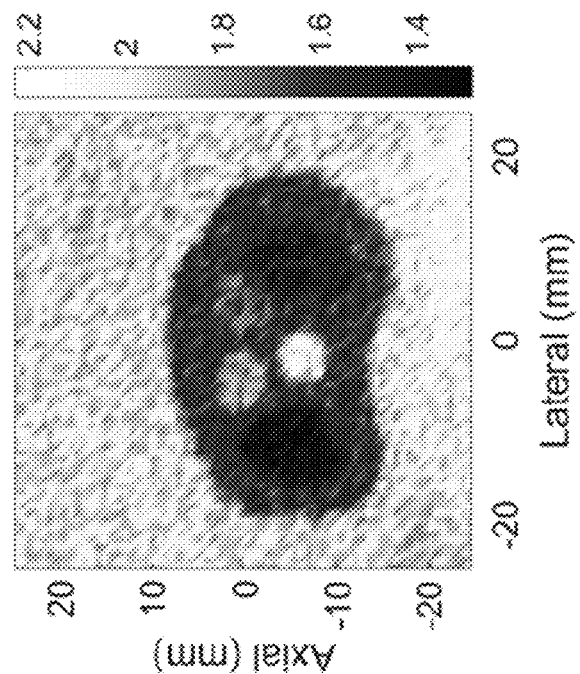
Figure 5:
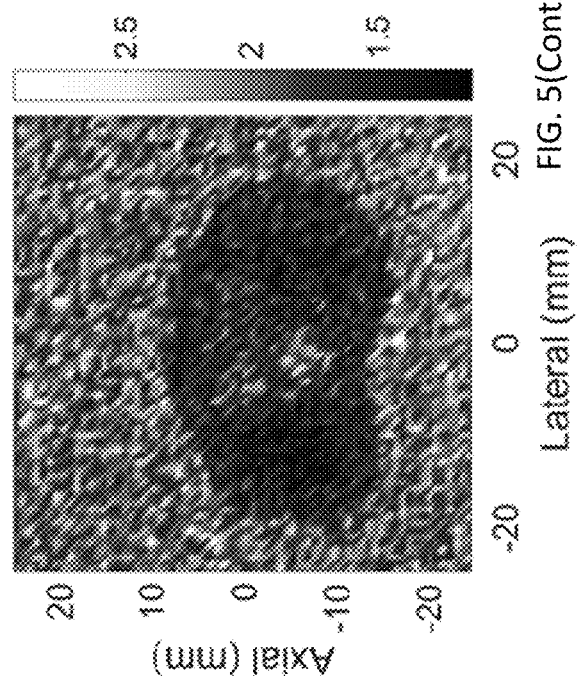
Figure 5:
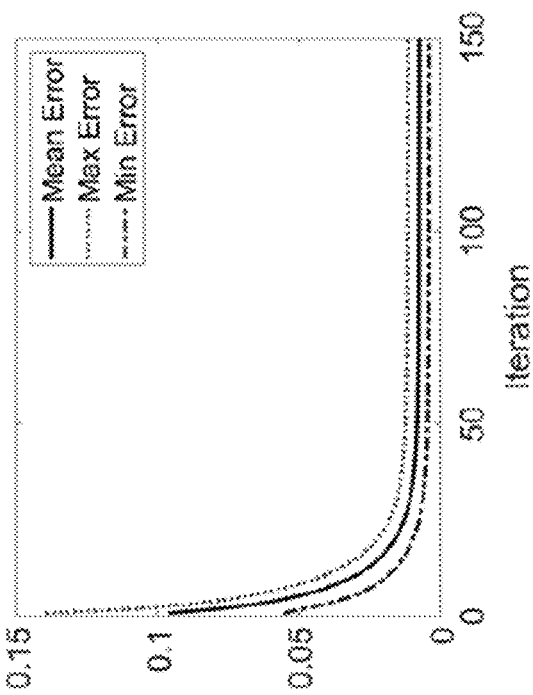
Figure 5:
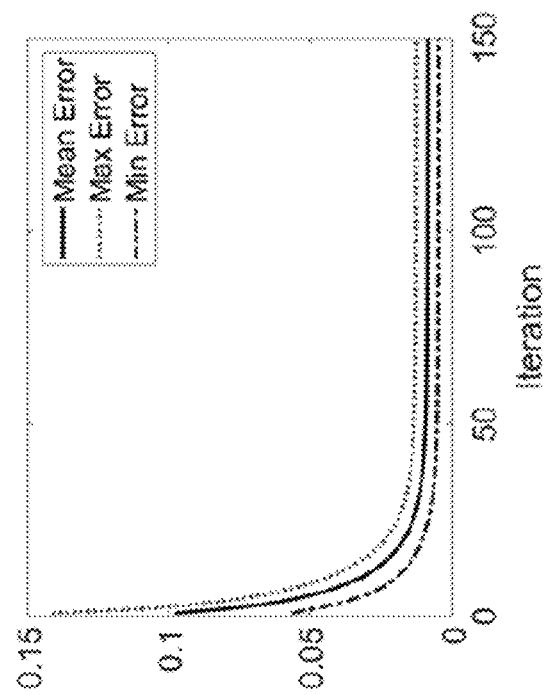
Figure 5:
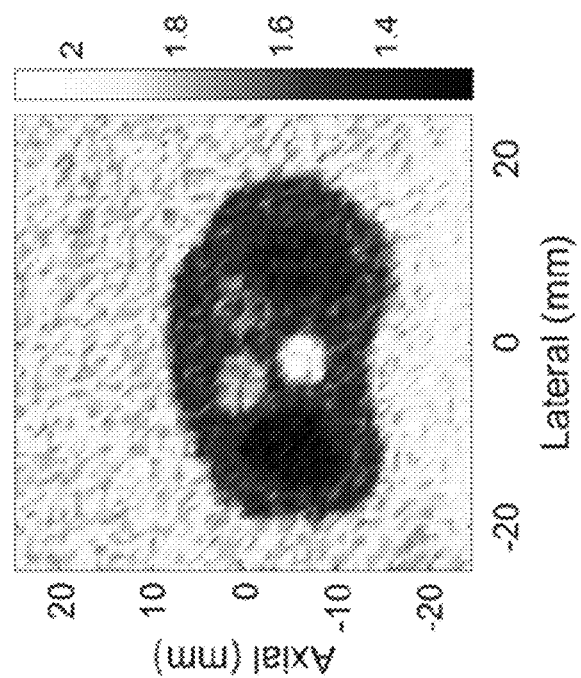
Figure 5:
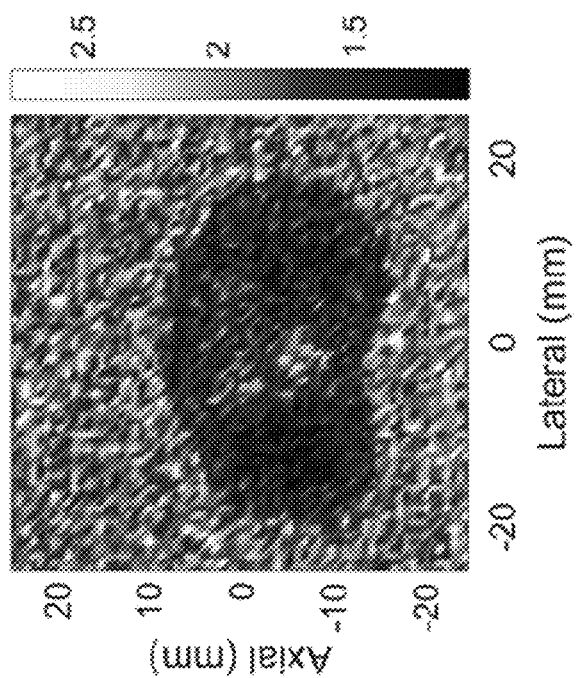
Figure 5:
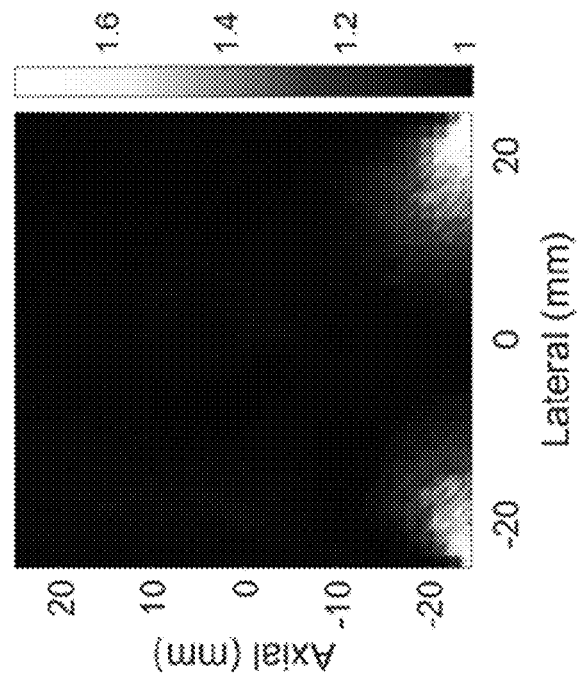
Figure 5:
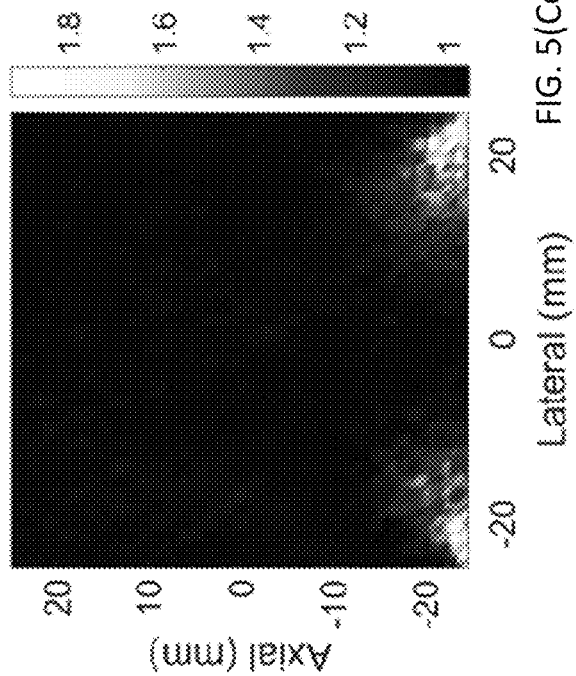
Figure 5:
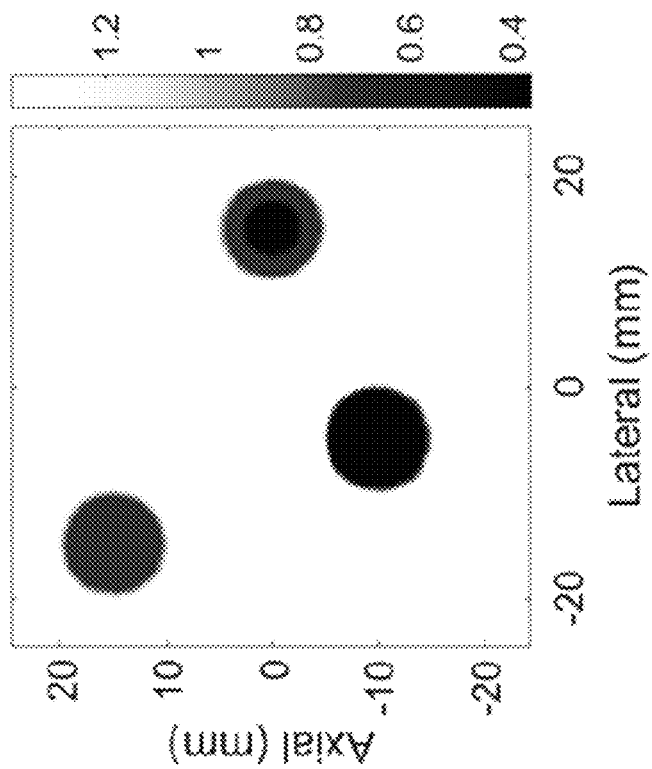
Figure 5:
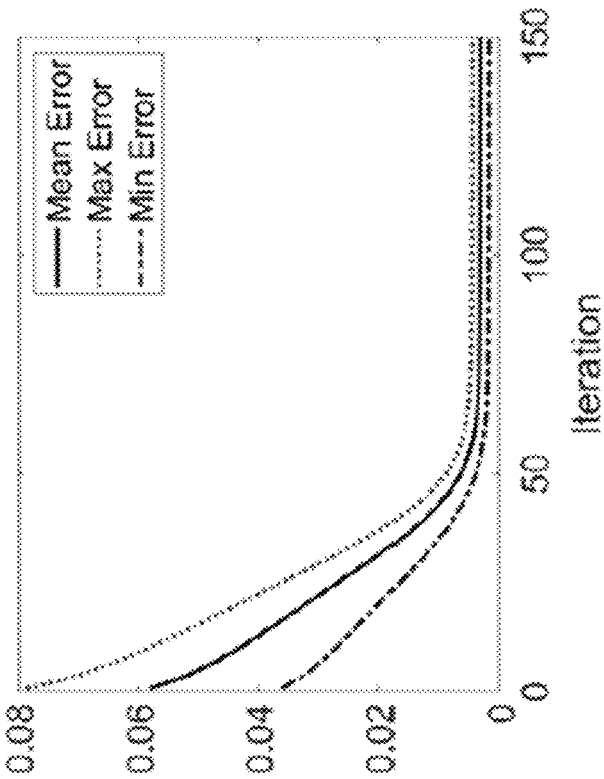
Figure 5:
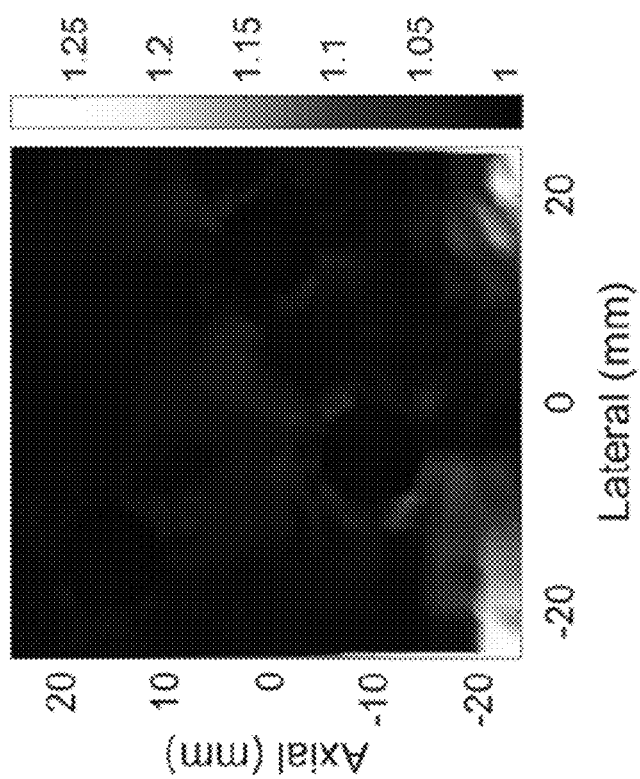
Figure 5:
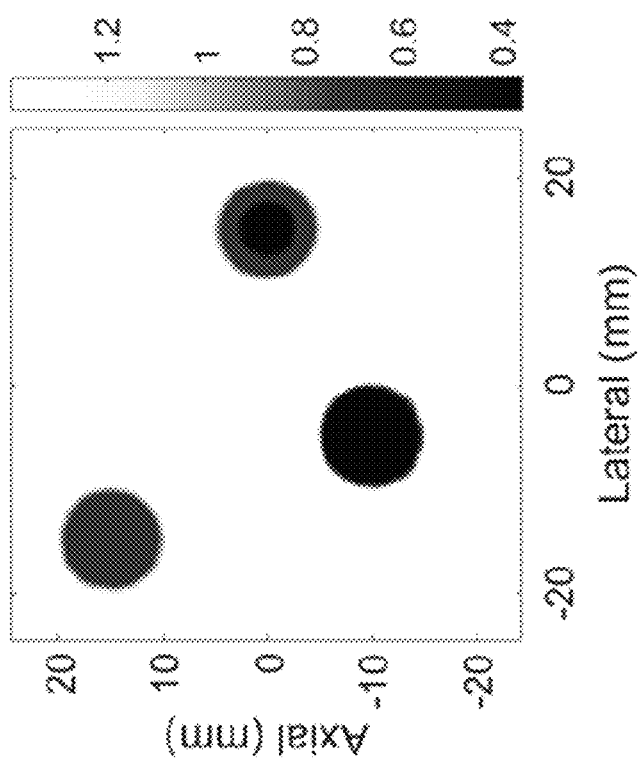

FIG. 5 provides the results of computing the spatial scaling values for all seven cases in this example. Plots in the left-most column are the mean, minimum, and maximum error in each iteration of Alg. 1. Errors are the root mean square (RMS) of the difference between $\sigma_t$ and $\sigma_i^{NN}$ over all stress-strain pairs for the model. Columns 2, 3, and 4 are the maps of $S_x^{\varepsilon_1}$, $S_x^{\varepsilon_2}$, $S_x^{\varepsilon_3}$ respectively.

The error curves provide insight on the number of iterations required in Alg. 1. When implemented in AutoP, the spatial scaling values will be recomputed many times, meaning there is a trade-off between computation speed and error. From these curves, 50 iterations appear to be sufficient, although other numbers may be employed. Images of the computed spatial scaling values, on the other hand, offer intuition on what information is contained with $S_x^\varepsilon$. The scaling values for the axial and lateral strains are inversely proportional to the Young's modulus. In the case of linear-elastic materials, the spatial scaling values, and thus the SN, contain information about distribution of the relative stiffness.

Figure 6:
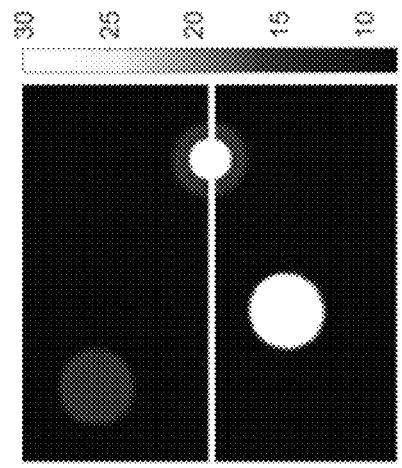
FIG. 6 illustrates a comparison of target and estimated Young's Modulus distributions in accordance with one or more aspects of the described technology.
Figure 6:
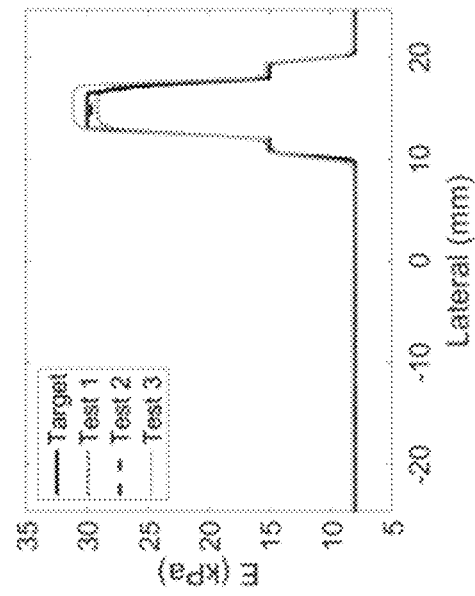
Figure 6:
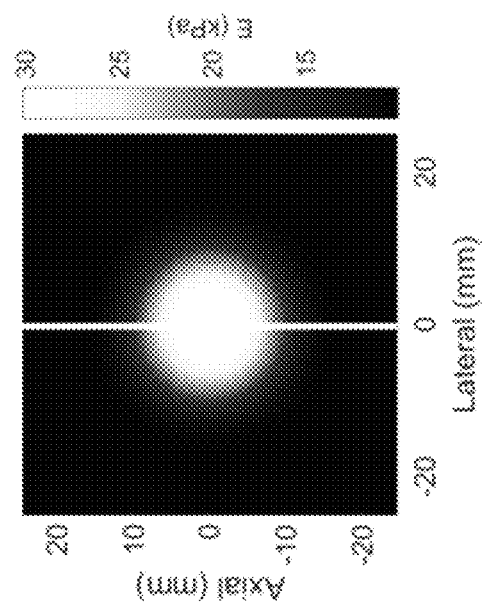
Figure 6:
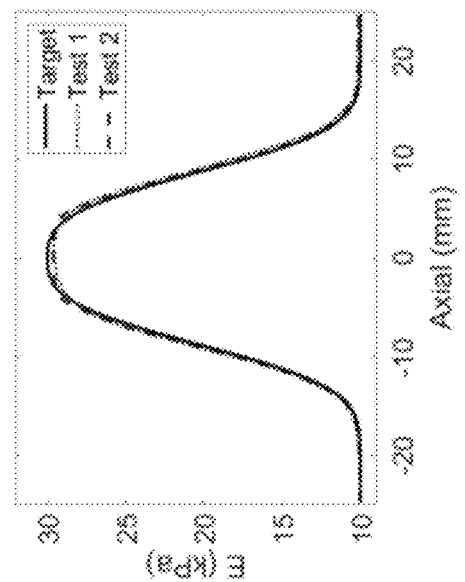
Figure 6:
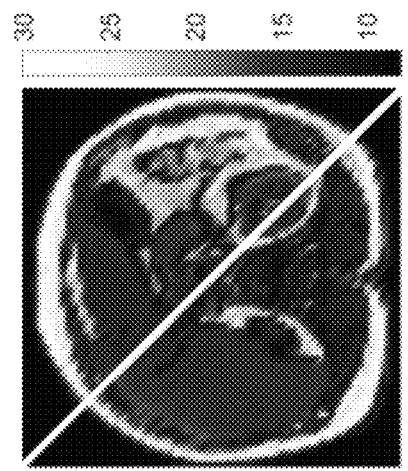
Figure 6:
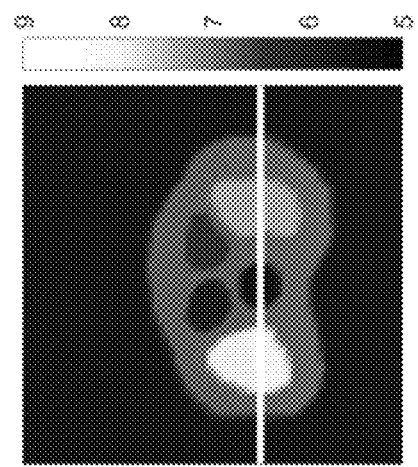
Figure 6:
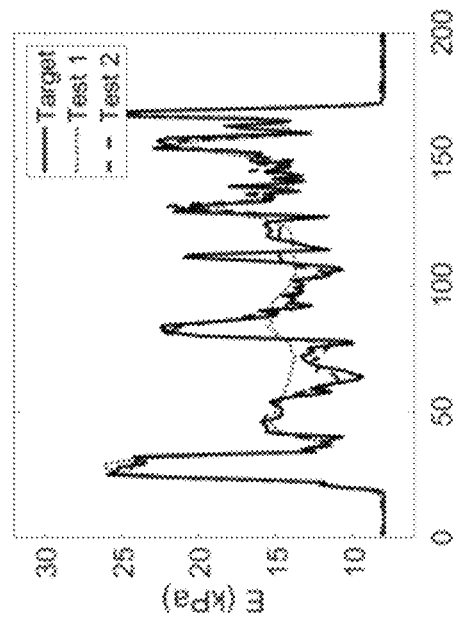
Figure 6:
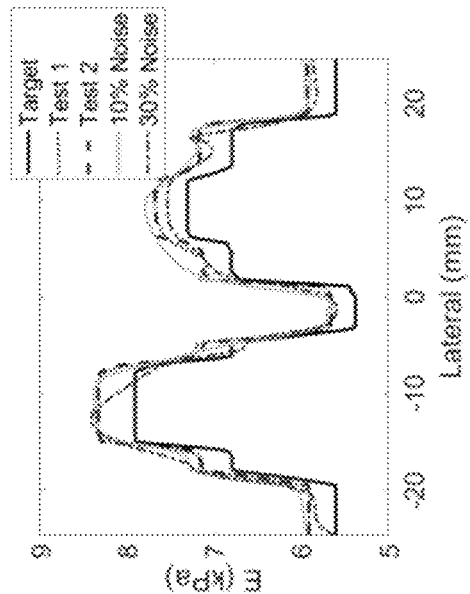

Young's modulus images reconstructed with CaNNCMs trained for the four models (no added noise and data generated on Mesh 1) are displayed in the middle and bottom rows of FIG. 4. A comparison of the target and CaNNCM-estimated Young's modulus along cross-sections of these two models are shown in FIG. 6. In the case of Model 1, there is no significant difference between the Young's modulus estimates between Test 1 and Test 2. Similarly, there is only a marginal difference in the results for Model 2. The effect of increased training iterations/epochs is far more pronounced for Models 3 and 4. In the case of the former, the boundaries of the regions become sharper. For Model 4, the internal structures only become distinguishable under Test 2 training.

Images reconstructed by CaNNCMs are expected to improve when the number of training epochs increases. That FIG. 4*l* better matches the target distribution than FIG. 4*h* is no surprise. These results show that 1) CaNNCMs are capable of learning fairly complex material property distributions and 2) in the absence of noise, the chosen training parameters do not result in over-training the SN.

Figure 7:
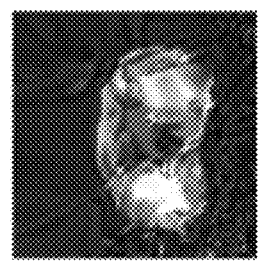
FIG. 7 illustrates Image reconstructions with CaNNCMs trained on data with 10% and 30% additive noise.
Figure 7:
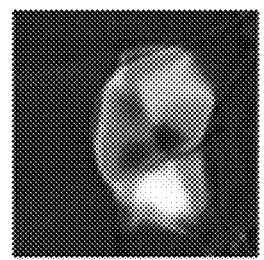
Figure 7:
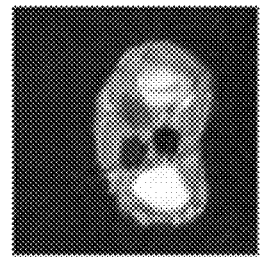
Figure 7:
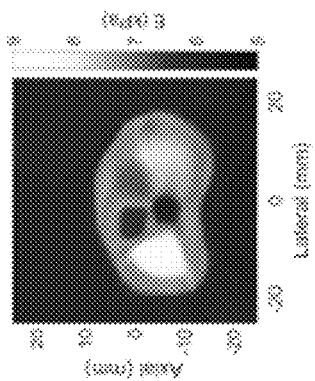

Image reconstructions with CaNNCMs trained on data with 10% and 30% additive noise are displayed in FIG. 7. Modulus values estimated along the line indicated in FIG. 6*c* by these CaNNCMs (trained with Test 1 parameters) are included in the curve comparison in FIG. 6*g*. The Young's modulus values computed by the CaNNCM trained on Model 2, Mesh 2, and Test 1 parameters along the line y=0 are included in FIG. 6*f*.

Table 1 contains quantitative comparisons between trained CaNNCMs and the target Young's modulus images. Training times for the SN are also included. For each point (x, y) in the mesh, the error between the target and CaNNCM Young's modulus estimate was computed using Eq. 14.

$$e_{(x,y)}^E = \frac{|E_{(x,y)}^{target} - E_{(x,y)}^{N,N}|}{E_{(x,y)}^{target}} \quad (14)$$

where $E_{(x,y)}^{target}$ is the target Young's modulus value at (x, y) and $E_{(x,y)}^{NN}$ is the modulus estimated by the corresponding trained CaNNCM.

TABLE 1

Young's modulus errors and SN training times for the four models shown in FIG. 4. No asterisk indicates Mesh 1, Test 1 parameters whereas single asterisk (*) indicates Test 2 parameters. The double asterisk (**) specifies the use of Mesh 2, Test 1 parameters

| Model | Modulus Error Mean ± STD | Training Time (s) |
| --- | --- | --- |
| 1 | 0.0166 ± 0.0099 | 71 |
| 1* | 0.0146 ± 0.0076 | 271 |
| 2 | 0.0131 ± 0.0172 | 71 |
| 2* | 0.0140 ± 0.0190 | 271 |
| 2.** | 0.0258 ± 0 0334 | 56 |
| 3 | 0.0504 ± 0.0142 | 72 |
| 3* | 0.0493 ± 0 0131 | 272 |
| 3 (10% noise) | 0.0534 ± 0.0198 | 71 |
| 3* (10% noise) | 0.0487 ± 0.0230 | 272 |
| 3 (30% noise) | 0.0418 ± 0.0252 | 71 |
| 3* (30%| noise) | 0.0549 ± 0.0399 | 271 |
| 4 | 0.0658 ± 0.0755 | 71 |
| 4* | 0.0485 ± 0.0518 | 270 |

As the complexity of the model geometry increases and training parameters remain the same, the mean error in the CaNNCM-reconstructed Young's modulus image also increases. Increasing the number training iterations and epochs in Test 2 generally reduced the error between target and CaNNCM-estimated values. The expectation was not met for Model 2 and Model 3 with 30% added noise. The increase in error for Model 2, Test 2 is likely a statistical artefact. Comparing the curves in FIG. 6f reveals the CaNNCM trained with Test 2 parameters better approximates the target curve. Furthermore, the images were interpolated to a new rectilinear grid before computing the error. It is possible that the interpolation procedure led the slightly increased error.

Over-training led to the increased error for Model 3 with 30% added noise. Comparing FIGS. 7c and 7d reveals the corruption was caused by the SN fitting the noise. Similarly, over-training may be also responsible for the increased error in Model 2 when Mesh 2, Test 1 parameters were used. The "Test 3" curve in FIG. 6f refers to this case and shows a slight bias in the Young's modulus estimate. A particularly large over-estimate occurs for the small, stiff inclusion embedded in the softer inclusion.

Biased errors also occur for Model 3 where all the CaNNCM-estimated Young's modulus values in FIG. 6g lie above the line denoting target modulus values. The same bias appears in all training cases for this model. While not displayed, this bias can be removed by pretraining the MPN as a 5 kPa linear-elastic material instead of 10 kPa. This should not be an issue when CaNNCMs are implemented in AutoP because the MPN may be retrained multiple times. Retraining the MPN with updated stress-strain data should alleviate these types of issues by adjusting the "reference" material to a form more suitable for the generated data.

CaNNCMs utilize two cooperating NNs to minimize the error between known and predicted stresses after a forward propagation of a strain vector and a (x, y) coordinate. The material property network learns a general stress-strain relation—here, the linear-elastic response of a 10 kPa homogeneous material—whereas the spatial network learns a map of relative stiffness.

Adding the spatial network required developing a method of computing its outputs. This may be realized by using a gradient-descent based approach by backpropagating the output error all the way to the MPN inputs/spatial network outputs. The spatial scaling values effectively encode stiffness relative to the reference material property. For example, $S_x^{\varepsilon_2}$ calculated for Model 1 is $\approx 0.3657$ at the 30 kPa inclusion peak and $\approx 1.1$ for the 10 kPa background, maintaining the ratio $30/10=1/3 \approx 1.1/0.3657$. Similarly, Model 4 values span 8-30 kPa and the resulting $S_x^{\varepsilon_2}$ are in the range [0.3891, 1.4014]. The spatial scaling values were not specifically computed to behave in this manner; this property emerged from minimizing the error function defined in Eq. 2.

Spatial networks tend to employ a larger network than MPNs. Increasing the number of hidden layers instead of vastly increasing the number of nodes per layer is a manner of increasing the network size. The mapping from (x, y) to $S_x^{\varepsilon}$ is more complicated than a linear stress-strain relationship and thus a network with larger capacity may be employed. While there is no strict rule for determining NN size, five hidden layers including 25 nodes each was sufficient for all four models in this study. However, the larger size of the SN increases the risk of over-training, as observed in Model 2 with 30% added noise.

Keeping the spatial network size constant, the Young's modulus reconstruction may be improved by changing the training parameters or the mesh. In the former case, increasing the number of epochs and training iterations produced better results by simply allowing more weight updates to occur. But increasing training epochs may increase training time. For the cases where Test 1 parameters were used, training time was $\approx 71$ s on a quad-core CPU operating at 2.7 GHZ. Test 2 parameters increased the time to $\approx 271$ s on the same computer.

Conversely, changing from Mesh 1 to Mesh 2 and resorting back to Test 1 parameters only used $\approx 56$ s of training time. Changing the mesh reduced the total number of data points from 4624 to 940, in turn reducing the training time. However, maintaining the same number of training epochs for the reduced amount of training data did not improve the resulting Young's modulus estimates. There was arguably a qualitative improvement due to changes in the data sampling distribution. With the rectilinear mesh, the edges of the inclusions are coarsely sampled and the number of data points pulled from the inclusions are small compared to the soft background material. Changing the mesh altered this sampling distribution so that data were better sampled around edges. While the addition of noise does not appear to significantly affect the ability of CaNNCMs to learn material properties, the geometry may be corrupted.

CaNNCMs may resolve fine structures with minor adjustments to training or the finite element mesh, the latter of which changes the distribution of available training data. CaNNCMs are fairly robust to noise and can still produce accurate estimates of Young's modulus for linear-elastic materials at the cost of geometric distortion. CaNNCMs incorporated into the Autoprogressive Algorithm, offer a machine-learning alternative to elasticity imaging.

Figure 8A:
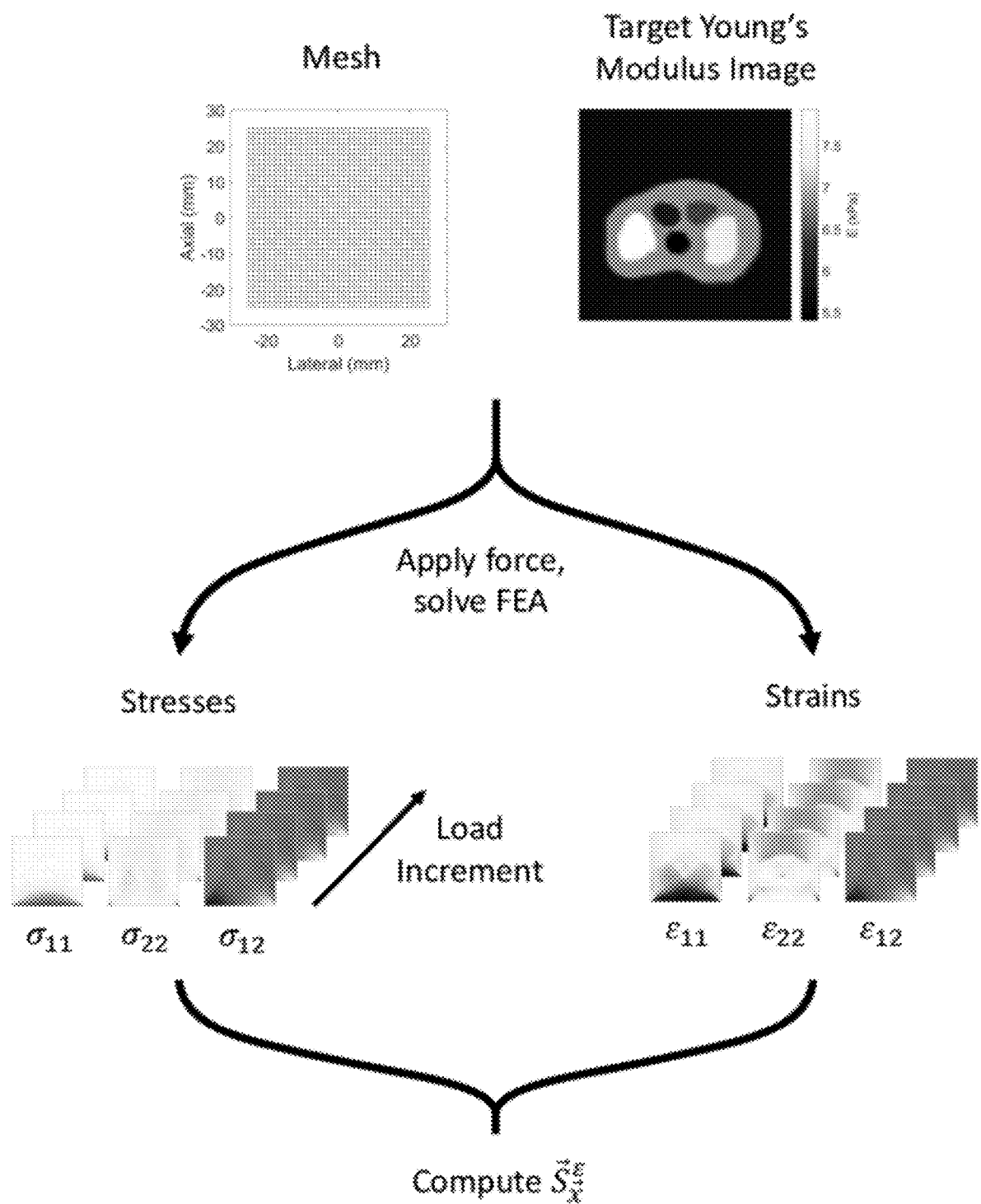
FIGS. 8A and B illustrate data generation techniques in accordance with one or more aspects of the described technology.
Figure 8A:
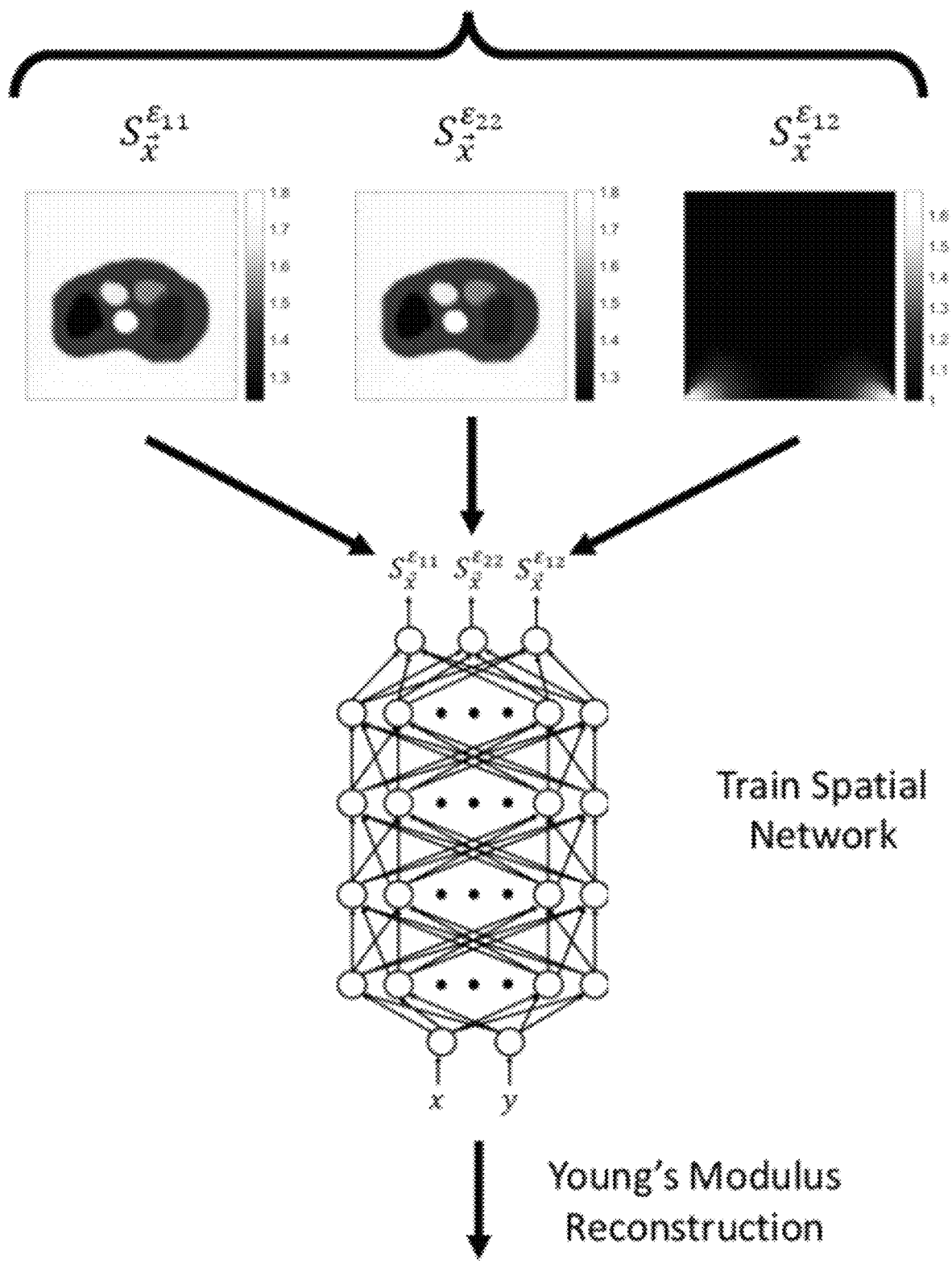
Figure 8A:
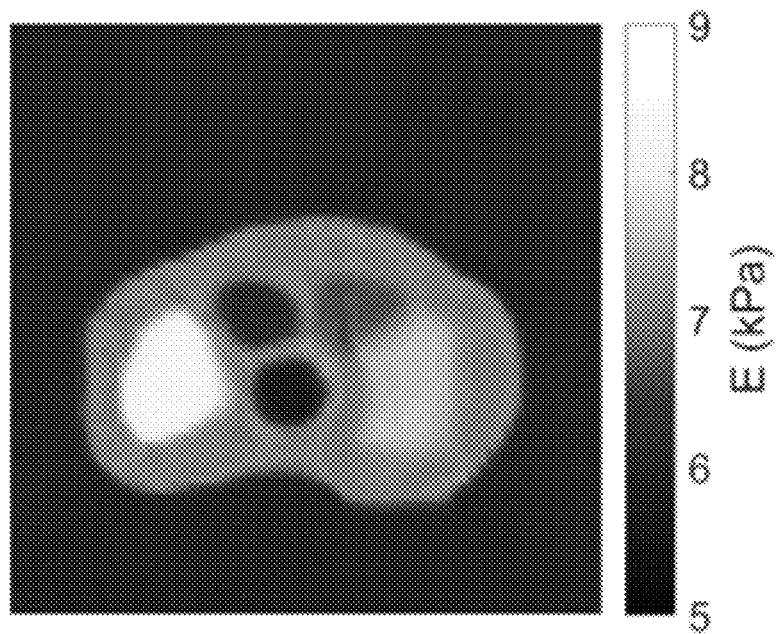
Figure 8B:
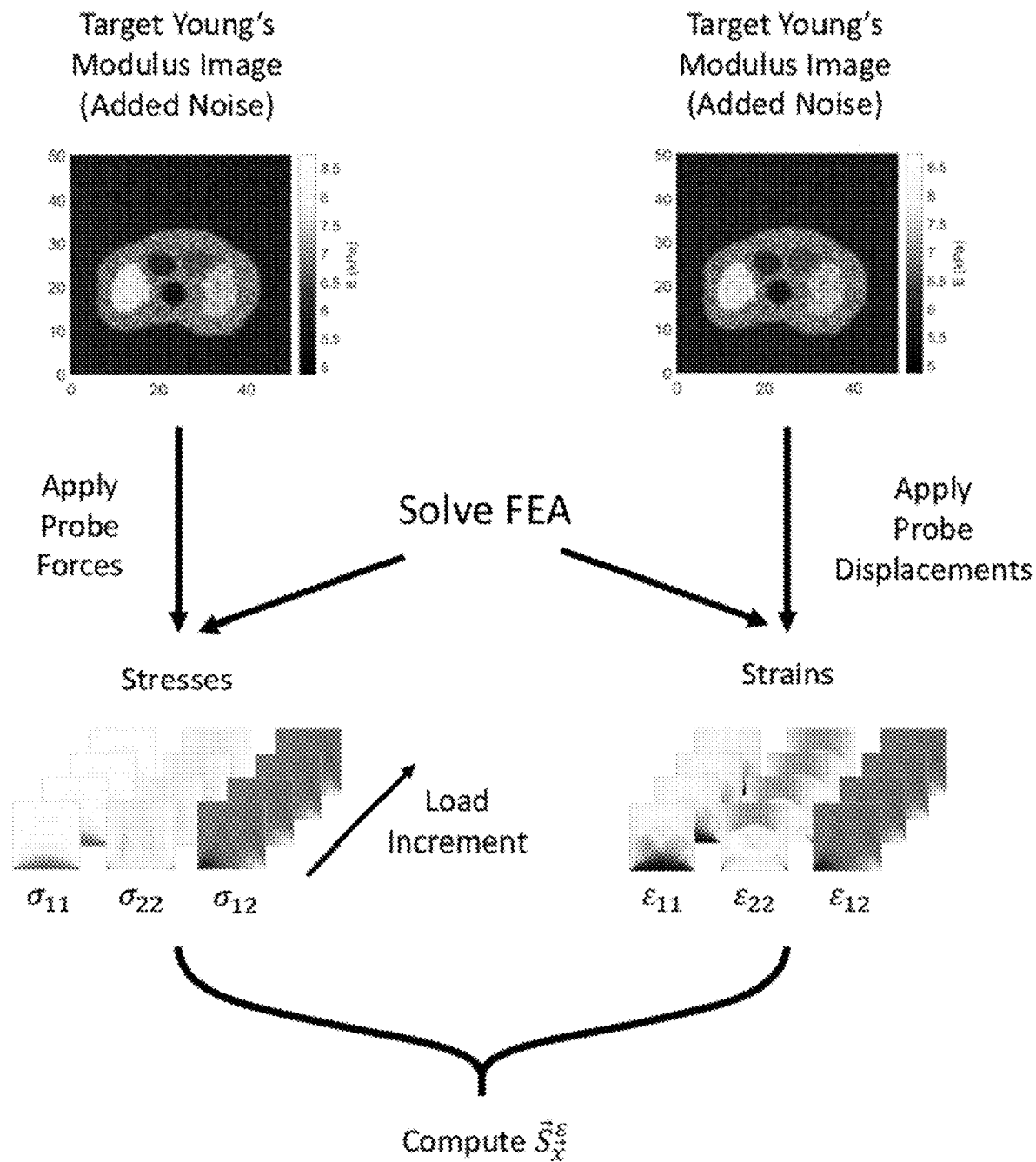
Figure 8B:
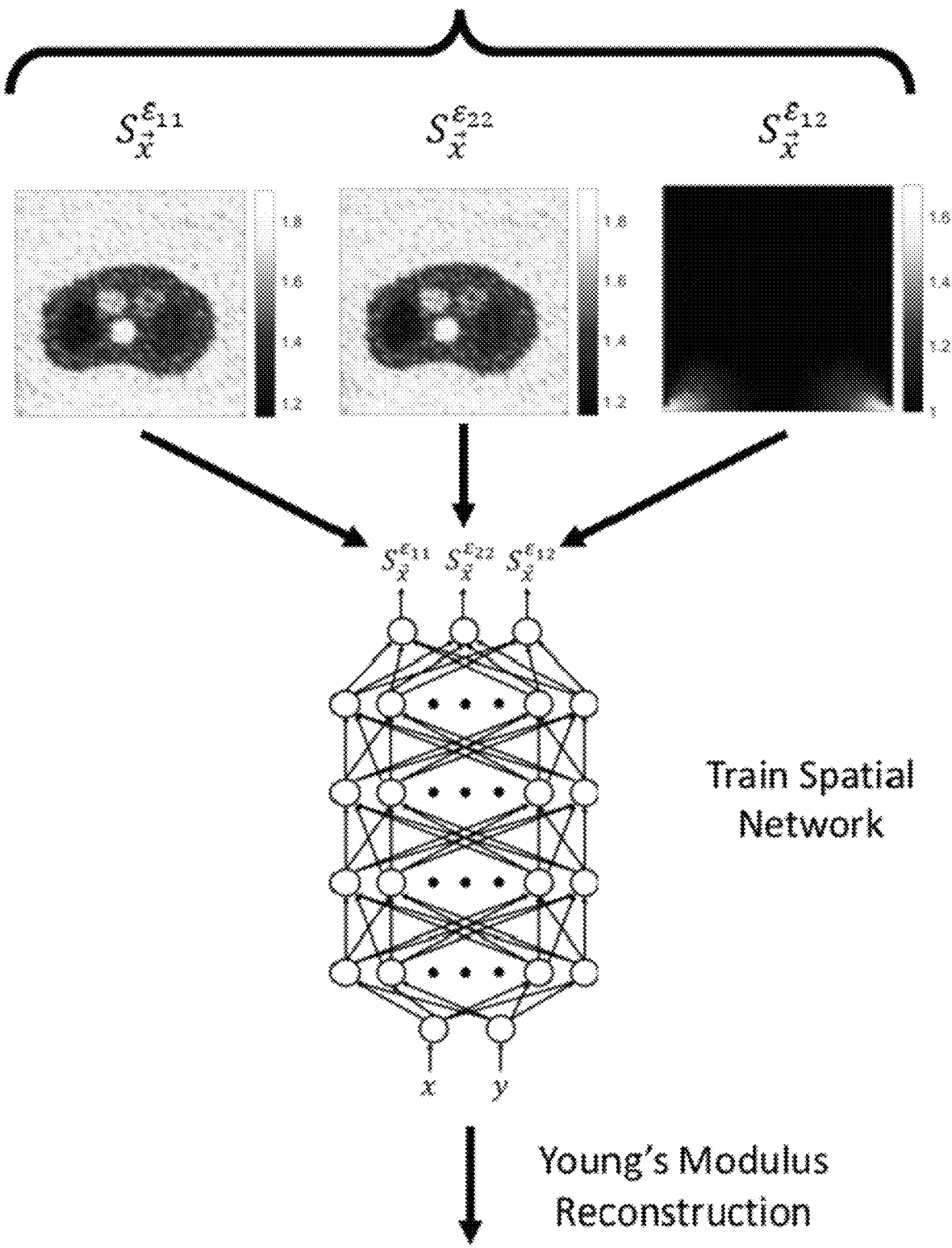
Figure 8B:
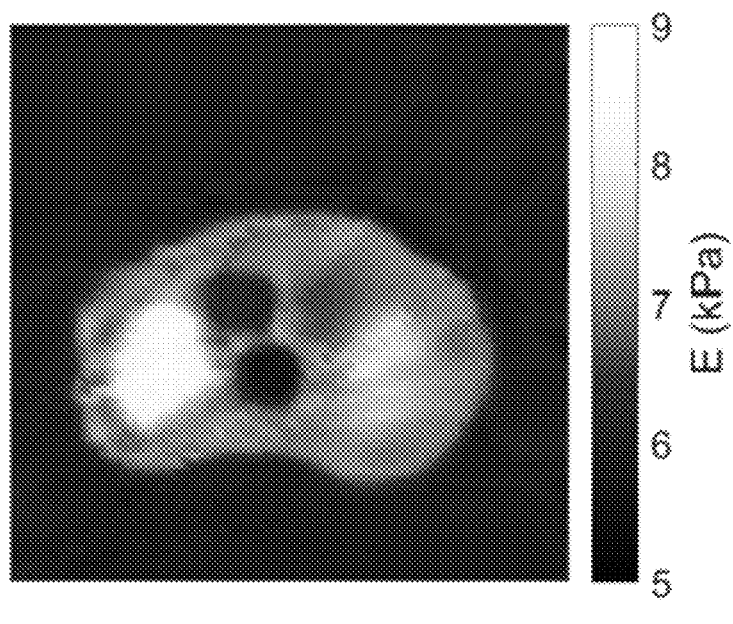

FIGS. 8a and 8b further illustrate the experimental procedure. When no noise was added to the target Young's modulus distribution, stresses and strains were both computed in a single FEA. Spatial scaling values were then computed using Alg. 1 and the pre-trained MPN. Conversely, two separate FEAs were solved to compute stresses and strains separately when noise was present. Noise was added by sampling from a zero-mean uniform distribution with maximum magnitude equal to either 10% or 30% of the Young's modulus at each x. For example, when 10% noise was added, the target Young's modulus at each point was E'(x, y)=E(x, y)+E(x, y)*p, where p∈[−0.1, 0.1]. Stresses and strains were computed in separate FEAs to avoid correlating the noise (i.e., the same value p was not used to compute E'(x, y) at each location).

The technology of this disclosure adopts a data-driven approach that first provides a nonparametric method for estimating stresses and strains from force and displacement measurements. Then, from stresses and strains, any and all models can be tested to find those parameters with significant diagnostic potential. The first steps in the development of our approach is disclosed in the co-pending application, using neural network constitutive models (NNCMs) and the Autoprogressive Algorithm (AutoP).

The architecture of a CaNNCM is depicted in FIG. 2A. It includes both a MPN 100 and spatial network (SN) 120. The structure and function of the MPN is unchanged, but the addition of the SN allows this pair of cooperating networks to learn spatially varying material properties. The MPN learns a "reference" stress-strain relationship whereas the SN learns how the object deviates from the reference as a function of position. Outputs from the SN are spatially varying strain scaling vectors, $S^\varepsilon \rightarrow S_x^\varepsilon$, meaning the SN transforms the strain vectors input to the MPN. The SN can be represented by the function $R_s: x \rightarrow S_x^\varepsilon$.

The MPN and SN together define the function $R_m, R_s$: $\varepsilon(x) \rightarrow \sigma(x)$. Image reconstruction occurs by relating the mechanical behavior learned by CaNNCMs to a chosen constitutive model after training. Even though modeling errors are still possible, a benefit lies in the potential for using a CaNNCM to estimate the parameters that might apply to any constitutive model. AutoP is used to minimize:

$$R_m, R_s = \underset{R_{\theta_m}, R_{\theta_s} \in \mathbb{B}}{\text{argmin}} \sum_{n=1}^{N_p} \sum_{k=1}^{N_d} f_u(u_k^n\{R_m, R_s\}, \hat{u}_k^n), \quad (15)$$

where $R_{\theta_m}$ refers to the weights of the MPN and $R_{\theta_s}$ are the weights of the SN. Here, $f_u(\bullet)$ is the L1 norm of the difference between measured $\hat{u}_k^n$ and computed displacements. L1 norm is used in this case rather than an L2 norm to reduce the effects of extensive outliers. This is minimized by reconciling stresses and strains estimated by the CaNNCM being trained. Then, using force-displacement measurements acquired through simulation and experimentally, it will demonstrate that CaNNCMs can learn stress and strain maps and ultimately reconstruct accurate Young's modulus images and explore how sampling affects the ability of CaNNCMs to learn these properties.

AutoP uses FEA to compute stresses and strains in response to force and displacement load increments. Internal $I^n$ and external $P^n$ forces are balanced for boundary conditions (BCs) applied in the nth load increment in the solution of a FEA:

$$P^n = I^n \quad (16)$$

$$I^n = I^{n-1} + K^n \Delta U^n \quad (17)$$

$$K^n \Delta U^n = P^n - I^{n-1} \quad (18)$$

$$K^n = \sum_{e=1}^{N_e} \int_{\Omega_e} B_e^T \overline{D^n(x)}^{CaNNCM} B_e d\Omega_e \quad (19)$$

$$I^{n-1} = \sum_{e=1}^{N_e} \int_{\Omega_e} B_e^T \overline{\sigma^{n-1}(x)}^{CaNNCM} d\Omega_e \quad (20)$$

where $K^n$ is the tangent stiffness matrix computed in the nth load increment, $\Delta U^n$ is the vector of displacement increments, $P^n$ is the vector of applied surface forces, and $I^n$ is the vector of internal resisting forces. In Eq. 18, $I^{n-1}$ is expressed as the sum over all Ne elements by multiplying the strain-displacement matrix Be with the stress vector $\sigma^{n-1}(x)$ and integrating over the element domains (e. Force BCs reside in $P^n$ and displacement BCs populate components of $\Delta U^n$.

A forward analysis includes applying force and/or displacement BCs to the FE model and solving the system of equations (18) for the unknown displacement increments that satisfy (16). During the analysis, the stiffness matrix $D^n(x)$ and stress vector are computed using a constitutive model or the CaNNCM. Both the stiffness matrix and stress vector in (19) and (20) are computed from the CaNNCM being trained, not a pre-selected constitutive model as would be done in model-based methods. The analytical expression for $D^n(x)$ is provided later in the discussion. FEA techniques are used to solve the forward problem for $u_n^k\{R_m, R_s\}$ in (15).

Figure 9A:
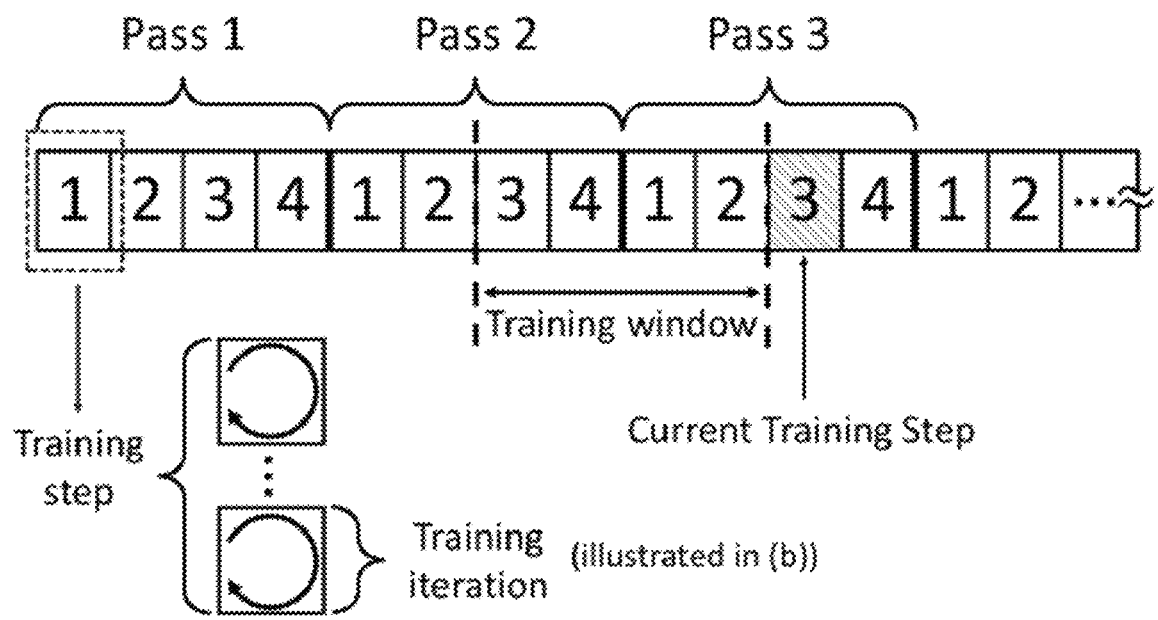
FIGS. 9A and B illustrates the training process of the Autoprogressive Algorithm in accordance with one or more aspects of the described technology.
Figure 9B:
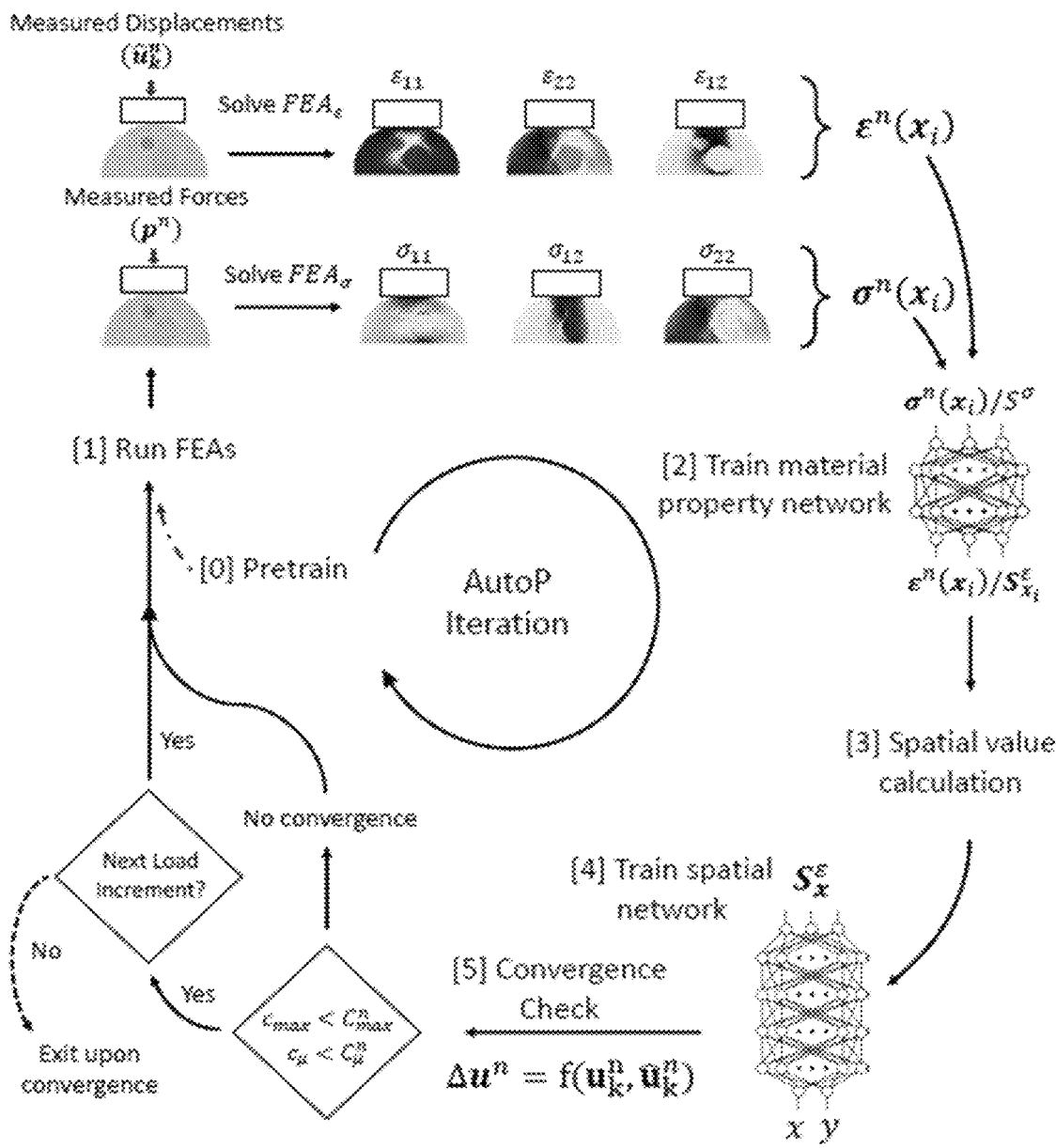

AutoP may be organized in a hierarchy of training passes, steps, and iterations as shown in FIG. 9a. A single training iteration may include several stages utilizing force-displacement measurements from a single load increment. A set of iterations performed with the same input measurement data may be a training step. Completing a series of training steps over all load increments may constitutes a pass. The following paragraphs track six stages of AutoP processing illustrated in FIG. 9b. AutoP iterations may be performed throughout training, during which the MPN and SN may be repeatedly retrained. The following considers the jth training iteration and introduces the superscripts j and j+1 to $R_m$ and $R_s$ to clarify which version of each network is active during each stage.

Pretraining (Stage [0]): Before the first set of measurement data is input, the CaNNCM may be initialized using linear-elastic equations (stage [0]). For the 2-D exemplary problems, a Young's modulus value and Poisson's ratio are chosen, a set of strain vectors are generated with randomly selected values over a small range. The corresponding stress vectors are computed using the plane-stress equation. Theoretically, any value of Young's modulus and Poisson's ratio can be selected for pre-training, although, as one might expect, accurate initializations result in faster convergence and avoids non-physical behavior in early FEA iterations. The stress scaling value and all spatial scaling vectors are set to one ($S^\sigma = 1$, $S_x^\varepsilon = 1$).

Estimation of stresses and strains (Stage [1]): Stage [1] includes estimating stresses and strains from measurement data. Forces for the nth load increment are applied to the FE model in $FEA_\sigma$. Referring back to (18), force measurements are imposed as BCs in $P^n$ and total mesh deformation is computed. Due to equilibrium conditions relating stresses to forces, all stresses $\sigma^n(x)$ computed throughout the model in $FEA_\sigma$ are assumed to be physically consistent estimates of the true stress. Similarly, in $FEA_\varepsilon$ US probe and internal displacement measurements from the nth load increment are input as components of $\Delta U^n$ to compute displacements of the remaining nodes. Due to compatibility conditions to relate node displacements to strains, the strains $\varepsilon^n(x)$ computed in $FEA_\varepsilon$ are assumed to be physically consistent estimates of the true strains. Recall that $R_m^j$ and $R_s^j$ are invoked by (19)-(20) to solve each FEA.

After estimating all stresses and strains, the stress scaling value $S^\sigma$ is checked to ensure all scaled stresses fall within ±0.8. It is checked if $\text{Max}(\sigma^n(x)/S^\sigma) > 0.8$, where the division is performed element-wise. If any component of $\sigma^n(x)$ falls outside this range, $S^\sigma$ is increased so that $\max(\sigma^n(x)/S^\sigma) = 0.8$.

Training MPN (Stage [2]): A total of $N_x$ stresses $\sigma^n(x_i)$ and strains $\varepsilon^n(x_i)$ are computed in $FEA_\sigma$ and $FEA_\varepsilon$, respectively. Each strain can by scaled by the corresponding $S_{x_i}^\varepsilon$, computed by $R_s^j$ and input to $R_m^j$ to compute a new stress $\hat\sigma^n(x_i)$. Stage [2] attempts to adjust the weights of the MPN to minimize the error between $\sigma^n(x)$ and $\hat\sigma^n(x)$:

$$R_m^{j+1} = \underset{R_m,\cdot\cdot}{\operatorname{argmin}} \sum_{i=1}^{N_x}\sum_{n=1}^{N_p}\sum_{l=1}^{N_\sigma} f_m\Big(\sigma_l^n(x_i),\, \overline{R_m^j\{\varepsilon_l^n(x_i),\, R_s^j(x_i)\}}\Big). \quad (21)$$

$R_s(x_i)$ is the output of the SN at $x_i$ and $N_\sigma$ is the number of stress-strains pairs at $x_i$ in the nth load increment. This value is greater than one when frame-invariance is enforced or a training window is implemented, both of which are described below. $f_m(\cdot)$ is the L2 norm of the difference between $\sigma^n(x)$ and $\hat\sigma^n(x)$; i.e., the MPN is trained via backpropagation.

Eq. (21) cannot be minimized to zero for a heterogeneous material given the current MPN architecture. As previously stated, the MPN accepts a single strain vector as input and responds with a single stress vector as output. There is a many-to-many mapping from $\varepsilon^n(x)$ to $\sigma^n(x)$ in heterogeneous materials. For example, in the case where $\varepsilon^n(x_i) = \varepsilon^n(x_j)$, it is not necessarily true that $\sigma^n(x_i) = \sigma^n(x_j)$ (i.e., $R_m$: $\varepsilon \to \sigma$ is not bijective). Thus, the SN supplies additional information in the form of $S_x^\varepsilon$ so that the MPN can determine which stress should be returned for a given strain.

Spatial scaling calculation (Stage [3]): The spatial values $S_x^\varepsilon$ are computed in stage [3]. While the coordinates input to the SN are given by the FE mesh, the target spatial values are determined based on $R_m^{j+1}$, $\sigma^n(x)$, and $\varepsilon^n(x)$. The error between $\sigma^n(x)$ and $\hat\sigma^n(x)$ may be further minimized by altering the spatial values instead of the weights of the MPN:

$$S_{x_i}^\varepsilon = \underset{S_x^\varepsilon}{\operatorname{argmin}} \sum_{n=1}^{N_p}\sum_{l=1}^{N_\sigma} f_m\Big(\sigma_l^n(x_i),\, R_m^{j+1}\{\varepsilon_l^n(x_i),\, S_{x_i}^\varepsilon\}\Big), \quad (22)$$

where $R_m^{j+1}$ is the output of the MPN retrained in (8).

[4] Training SN: With a complete set of training data, the SN is trained in stage [4] via backpropagation:

$$R_s^{j+1} = \underset{R_s,\cdot\cdot}{\operatorname{argmin}} \sum_{n=1}^{N_p}\sum_{i=1}^{N_x} f_s\Big(S_{x_i}^\varepsilon,\, R_s^j\{x_i\}\Big). \quad (23)$$

Convergence check (Stage [5]): Finally, a convergence check is performed in stage [5] to determine if training iterations for the current step should continue. Node displacements $u_k^n$ computed in $FEA_\sigma$ are compared to the measured displacements $\hat u_k^n$ using the $L_1$ norm of their difference:

$$\Delta u_k^n = |u_k^n - \hat u_k^n| \quad (24)$$
$$= f_u(u_k^n\{R_m, R_s\}, \hat u_k^n)$$

which is the objective function defined in (15). Only axial displacements have been disclosed, although lateral and/or elevational displacements can also be used if available.

Following previous implementations of AutoP to determine NNCM convergence, displacement errors are used to compute two new values:

$$\hat c_{max}^n = \frac{\max(|\Delta u_k^n|)}{|\max(|u_k^n|)|}$$

$$\hat c_\mu^n = \frac{\operatorname{mean}(\Delta u_k^n)}{|\max(|u_k^n|)|}$$

Convergence criteria $C_{max}^n$ and $C_\mu^n$ are defined for the nth training step. If both $\hat c_{max}^n < C_{max}^n$ and $\hat c_\mu^n < C_\mu^n$, convergence has been achieved and AutoP training iterations may stop for the current training step. Otherwise, iterations of stages [1]-[5] may continue until the convergence criteria are met or a maximum number of iterations are reached. Training steps continue for each increment of force-displacement data in the set to complete a pass. Multiple passes are typically employed to ensure the CaNNCM has fully learned the material behavior. A CaNNCM is not expected to accurately model the material properties in the first few passes. Therefore AutoP may begin with relaxed convergence criteria (larger values of $C_{max}^n$ and $C_\mu^n$) that gradually become more restrictive.

An imaging phantom was constructed from a mixture of deionized water, gelatin powder, and cornstarch acting as a scattering agent. The phantom included a 50×50×50 mm³ cube of a soft background gel ($\approx$7.15±0.18 kPa, 8% gelatin by mass) with three stiff, cylindrical inclusions. Each inclusion was 10 mm in diameter and 50 mm long. Mechanical contrast was controlled by the ratio of gelatin to water and each inclusion was a different stiffness ($\approx$10.93±0.57, 14.15±0.71, or 20.51±0.84 kPa, 10%, 12%, and 14% gelatin by mass, respectively). The phantom was manufactured in the same manner described in the co-pending application and separate samples of each gelatin mixture were stored to independently estimate Young's modulus values via macro-indentation methods.

Figure 10:
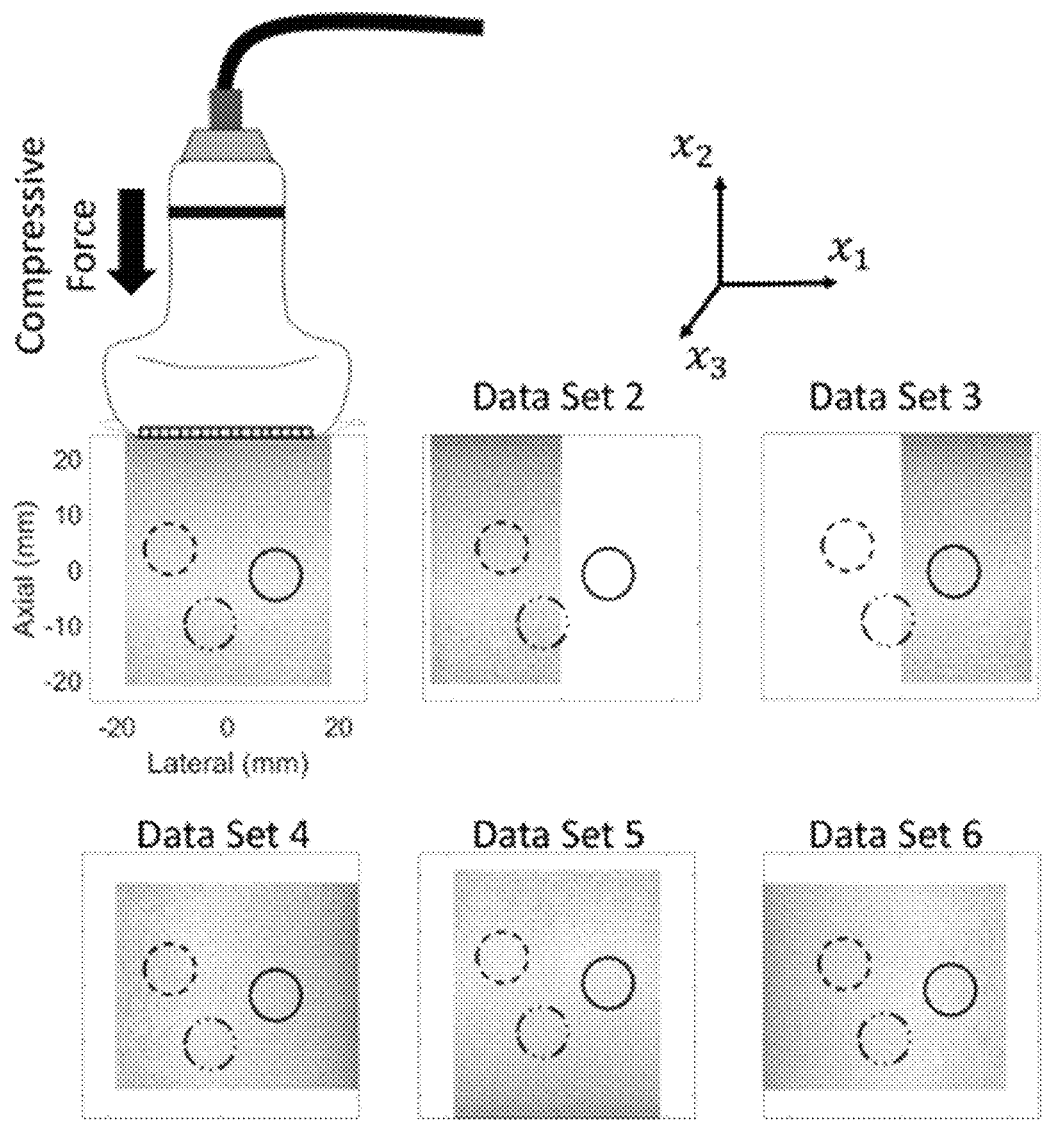
FIG. 10 illustrates six different data sets collected in accordance with one or more aspects of the described technology.

Compressive loads were applied to the phantom over four equal axial displacement increments of the US probe. Total probe motion was 1.44 mm, 3% of the pre-loaded phantom height. After applying each load increment, axial force and probe position were measured and an RF echo frame was acquired. The speckle-tracking algorithm GLUE was applied to the echo data to estimate axial displacements in the field of view. Axial forces, probe displacements, and internal displacements over all four load increments constitute one set of force-displacement data. FIG. 10 shows six different data sets collected. Sets 1-3 were all acquired by compressing down-ward onto the top surface but with different lateral placements of the US probe. Sets 4-6 were acquired by keeping the probe centered laterally, but rotating the phantom 90°, 180°, and 270° around $x_3$, respectively. Two additional data sets were acquired where the imaged regions were centered on the $x_2$ axis like Data Set 1, but the probe moved in elevation, along $x_3$, by ±4 mm. These data sets are referred to as Data Set 1' and 1", respectively. Total forces applied by the US probe ranged from 17.95 to 21.22 mN.

A simple FE model was created for use in AutoP and to generate the noise-free data sets described in the next section. The FE model FEM-1 is a 2-D, rectilinear FE mesh with 50 nodes per edge (FIG. 11) to represent the phantom. The ultrasound probe was modeled as a rigid body in frictionless contact with the top surface of the phantom model, approximating the condition created by the US gel. The bottom nodes of the phantom mesh were fixed to mimic contact between the gelatin phantom and rubber pad. The full mesh included 2516 nodes (5032 DOF) and 2401 plane-stress elements (CPS4 in Abaqus 6.13). Given that 4-node quadrilateral elements contain four integration points, a total of 9604 stress-strain pairs are computed in each of two FEAs, labeled FEA$_\sigma$ and FEA$_\varepsilon$, which are described above. Force loads, when applied as boundary conditions (BCs) in FEA$_\sigma$ or in a forward problem, were defined as concentrated forces to the top of the probe model. Similarly, probe displacements in FEA$_\varepsilon$ were defined as BCs for the entire probe model. Note that FEM-1 refers to the mesh and method of applying BCs. All FEAs were solved with ABAQUS 6.13 commercial finite element software.

First, AutoP employing CaNNCMs and noise-free force and displacement data was tested. Three different material property distributions (FIGS. 12a-c) were created to generate simulated measurements. Model 1 includes a stiff Gaussian-shaped inclusion with a peak stiffness of 30 kPa embedded in the center of a 10 kPa background. Model 2 was a replicate of the gelatin phantom described previously. Young's modulus values for the background and three inclusions were selected to be the same as those estimated via macro-indentation for each gelatin material. Model 3 corresponded to a rabbit kidney embedded in a block of gelatin with background Young's modulus 5.61 kPa. Modulus values for the kidney were based on previous results using AutoP and linear-elastic MPNs. Models 1 and 3 were chosen to enable comparison with results reported earlier where stress-strain data were known.

Force-displacement data were generated by solving a forward FEA using FEM-1 and the target Young's modulus distributions of Models 1-3. The same forces and loading geometry of Data Set 1 were applied to the model and displacements were computed at all nodes. Each simulated data set contained noise-free data over four load increments.

Simulated RF echo frames were generated to test the capabilities of CaNNCMs in the presence of noise. A detailed description of the method used to generate these images is provided below. The two simulated sets were intended to emulate Data Set 1 with different SNR in the RF echo data: one with 30 dB SNR and one with 15 dB SNR. The former is referred to as Data Set 1$^\dagger$ and the latter as Set 1$^{\dagger\dagger}$.

CaNNCMs were trained in AutoP using force-displacement data obtained in three ways. First, forward FE modeling simulated noise-free displacements at each node in the FE mesh. Second, the same simulated displacements were entered into an RF echo simulator to simulate noisy experimental data. Both data sets have exactly-known displacements and material properties. Third, RF echo signals were recorded experimentally from phantoms. All tests used the same training parameters described below. Any differences in how CaNNCMs were trained lie in how the force-displacement data were sampled. Changes to the input data do not imply a need to alter training parameters.

Several different training cases were used that differed in the number of axial displacements applied in FEA$\varepsilon$. Table I summarizes these four cases.

TABLE I

Figure 11:
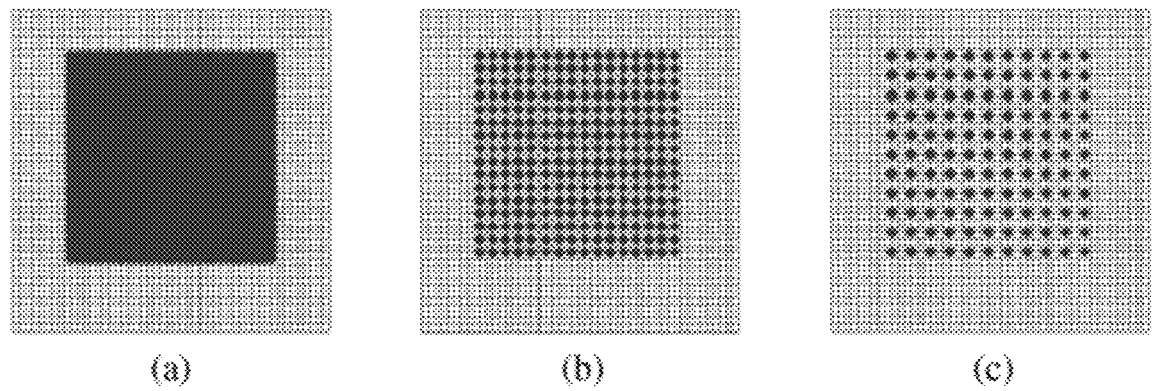
FIG. 11 illustrates 2-D, rectilinear FE mesh with 50 nodes per edge in accordance with one or more aspects of the described technology.

FOUR CASES FOR APPLYING AXIAL DISPLACEMENTS IN AUTOP. CASES 2-4 ARE ILLUSTRATED IN FIG. 11.

| case 1 | All nodes in mesh |
| case 2 | All nodes in ROI < mesh size |
| case 3 | Node in ROI, 1.5 mm minimum separation |
| case 4 | Nodes in ROI, 3 mm minimum separation |

For case 1, displacements are given at every node in the mesh. Cases 2-4 only used displacements in the ROI. The ROI is the region corresponding to the size of the displacement image after speckle-tracking was applied to the RF frames. Case 2 (FIG. 11, (a)) indicates all nodes in the ROI were assigned displacements. For Cases 3 and 4 (FIGS. 11b and c, respectively), axial displacements were only given at nodes with a minimum separation of 1.5 mm and 3 mm, respectively. These are the variable sampling settings selected to explore the role of displacement sampling in AutoP convergence.

Upon completion of AutoP, each CaNNCM was used to reconstruct a map of the Young's modulus distribution. Image reconstruction was performed by setting a constant strain vector $\varepsilon=[0.003\ 0.005\ 0.0001]$ and computing the stiffness matrix $\hat{D}_{ij}$ using (eq. 30 below). The Young's modulus distribution $E(x)$ was then estimated by varying $x$ in the domain of the mesh and evaluating the function:

$$E(x) = \frac{\sigma}{S_x^{\varepsilon_3}} \hat{D}_{22}(1 - v^2), \quad (27)$$

where $v=0.5$ and $S_x^{\varepsilon_2}$ is the axial component of the spatial scaling vector at $x_i$. The choice of constant strain vector is not important so long as it resides within the range of training data. Small values for each component were selected to ensure the strain was within range, and the axial strain was emphasized and $D_{22}$ was used in the modulus estimate because the models were axially compressed.

Figure 12:
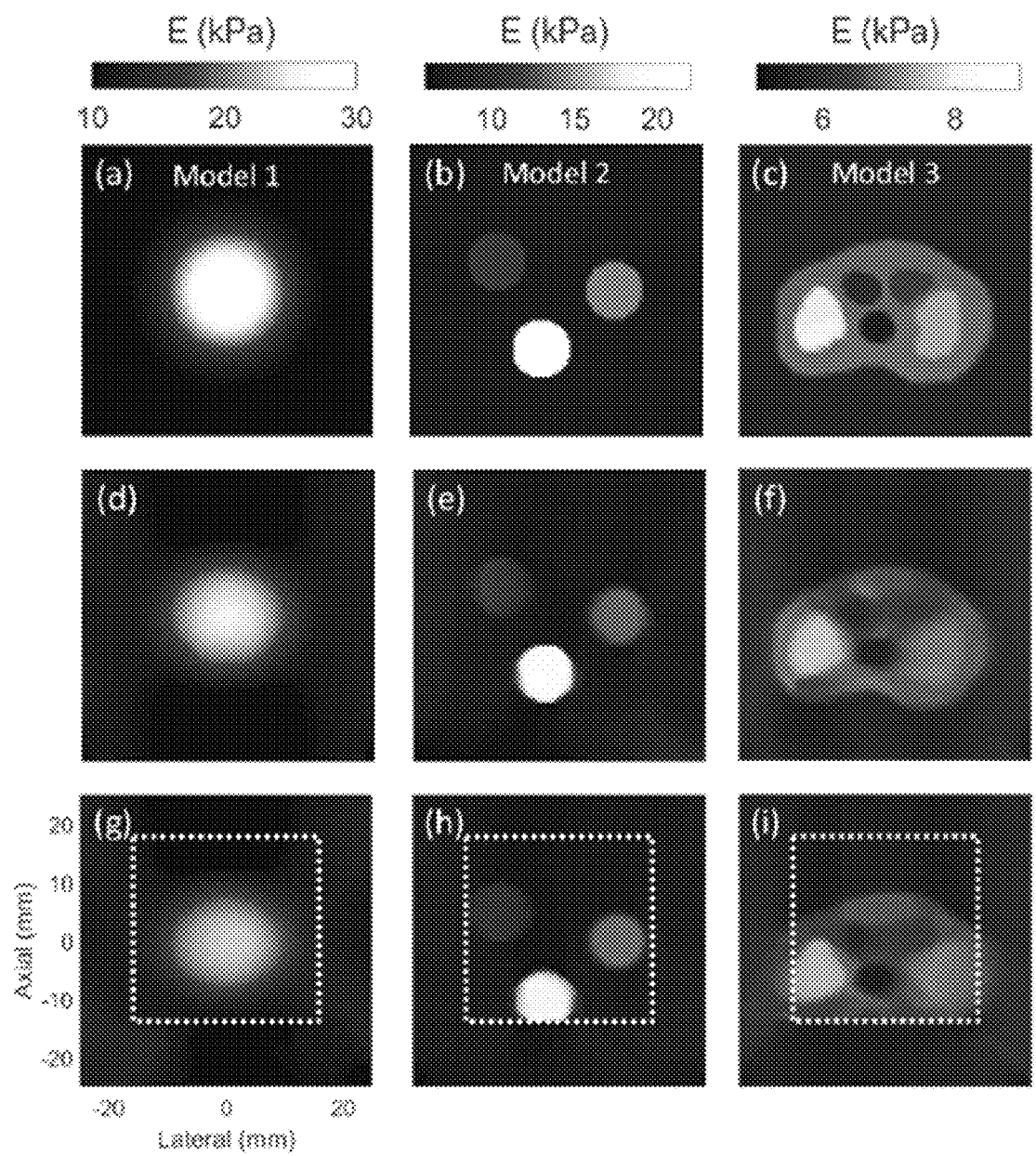
FIG. 12 illustrates a comparison of target and estimated Young's modulus distributions for three different models.

Young's modulus distributions estimated by the CaNNCMs were compared to the target maps shown in the top row of FIG. 12. Errors were computed as:

$$e_x^E = \frac{|E_x^{target} - E_x^{NN}|}{E_x^{target}}$$

where $E_x^{target}$ is the target Young's modulus distribution and $E_x^{NN}$ is the CaNNCM estimate. Because displacements are only provided in the field of view for Cases 2-3, CaNNCM is not expected to accurately estimate Young's modulus values outside of the ROI where no displacement measurements are acquired. Therefore $e_x^E$ is computed only within the ROI for all cases.

The following describes each of the CaNNCMs being trained. Simulated Force-Displacement Data: A total of six CaNNCMs were trained in AutoP using noise-free force-displacement data generated from the three simulated models. One network was trained for each model using Case 1 and Case 2 displacement sampling. The results from training these networks demonstrate the ability of CaNNCMs to learn material properties when the sampling space is reduced.

Simulated RF Echo Data: Another six CaNNCMs were trained using force-displacement data gathered from the simulated RF echo frames with varying amounts of echo noise. Three CaNNCMs for Data Set $1^{\dagger}$ and three for Set $1^{\dagger\dagger}$ using Cases 2-4 sampling distributions. Results from these analyses demonstrate how reducing the number of sampling points affects the ability of CaNNCMs to learn material properties and geometry in the presence of noise.

Gelatin Phantom: 12 CaNNCMs were trained with experimental measurement force-displacement data. The first three were trained with Data Set 1 and sampling Cases 2-4. Results obtained from these CaNNCMs and those trained with data acquired via the simulated RF data guided the choice of sampling for the remaining CaNNCMs. Using Case 3 sampling, one CaNNCM was trained with each of Data Sets 2-6, 1', and 1", one with Sets 1-3 simultaneously, and one with Sets 1, 1', and 1" simultaneously. Results from these CaNNCMs demonstrate the ability of CaNNCMs to learn material properties under different loading scenarios, how the inclusion of multiple independent data sets affects the Young's modulus estimates, and how sparser sampling influences the learned material and geometric properties.

Results: Young's modulus images reconstructed by CaNNCMs trained with noise-free force-displacement data are displayed in FIG. 12. Errors in the modulus estimates computed with (28) are compiled in Table II for all CaNNCMs. Also included in the table are the processing times and total number of AutoP training iterations performed.

TABLE II

Figure 15:
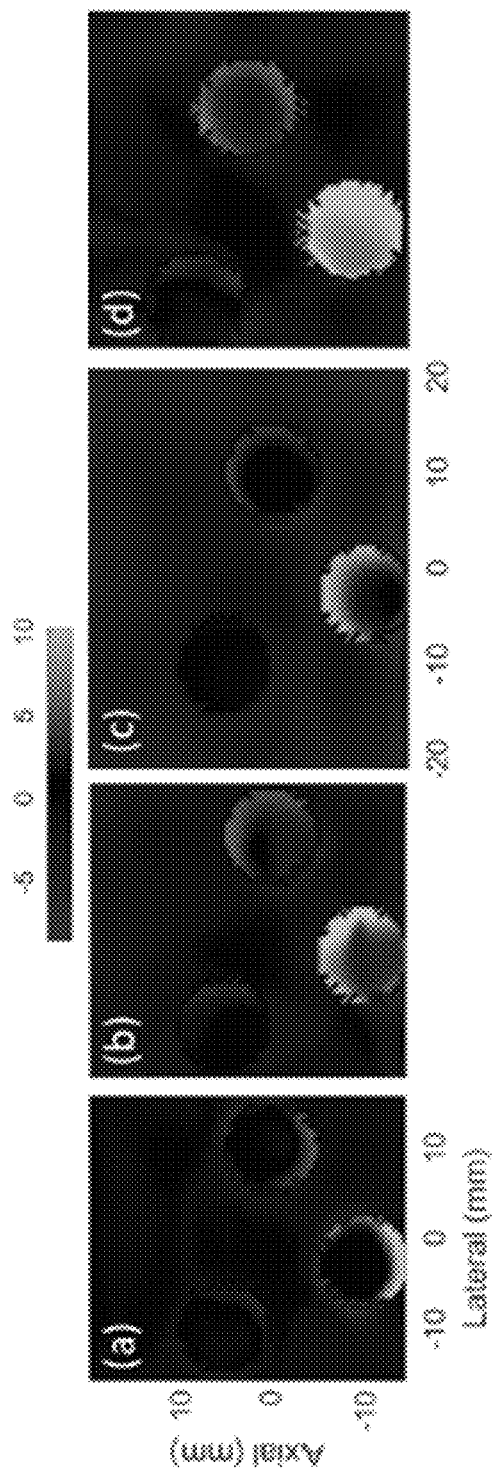
FIG. 15 illustrates images of the Young's modulus error generated by computing differences between target and reconstructed Young's modulus images.

YOUNG'S MODULUS RECONSTRUCTION ERRORS AND AUTOP RUN TIME. MODELS ARE ILLUSTRATED IN FIGS. 12A-C. SETS ARE ILLUSTRATED IN FIG. 3. CASES ARE DESCRIBED IN TABLE I. SIMULATED RF DATA SETS WITH 30 DB AND 15 DB SNR ARE DENOTED † AND ††, RESPECTIVELY. A SUPERSCRIPT LETTER INDICATES SUBFIGURE IN FIG. 15. THE LAST COLUMN INDICATES THE FIGURE NUMBER OF THE CORRESPONDING YOUNG'S MODULUS IMAGE.

| (Model #){Set}[case] | Modulus Error Mean ± STD | Time (min.) | Iters. | FIG. |
|---|---|---|---|---|
| Simulated Force-Displacement | | | | |
| (1){1}[1] | 0.1055 ± 0.0545 | 151 | 74 | 5d |
| (1){1}[2] | 0.1349 ± 0.0670 | 153 | 75 | 5g |
| (2){1}[1] | 0.0621 ± 0.0730 | 88 | 42 | 5e |
| (2){1}[2] | 0.0643 ± 0.0690 | 82 | 46 | 5h |
| (3){1}[1] | 0.0306 ± 0.0188 | 83 | 40 | 5f |
| (3){1}[2] | 0.0370 ± 0.0211 | 80 | 40 | 5i |
| Simulated RF | | | | |
| (2){1†}[2] | 0.0961 ± 0.1240 | 80 | 40 | 6a |
| (2){1†}[3] | 0.1325 ± 0.1294 | 79 | 40 | 6b |
| (2){1†}[4] | 0.0970 ± 0.1126 | 82 | 42 | 6c |
| (2){1††}[2] | 0.0914 ± 0.1336 | 80 | 40 | 6d |
| (2){1††}[3][a] | 0.0899 ± 0.1111 | 110 | 56 | 6e |
| (2){1††}[4] | 0.1386 ± 0.1313 | 90 | 46 | 6f |
| Gelatin Phantom | | | | |
| (2){1}[2] | 0.2136 ± 0.1264 | 139 | 69 | 6g |
| (2){1}[3][b] | 0.2736 ± 0.1563 | 136 | 69 | 6h |
| (2){1}[4] | 0.3168 ± 0.1784 | 136 | 69 | 6i |
| (2){1'}[3] | 0.2604 ± 0.1576 | 139 | 69 | 7a |
| (2){1"}[3] | 0.2522 ± 0.1480 | 138 | 69 | 7b |
| (2){2}[3] | 0.1828 ± 0.1175 | 138 | 69 | 7d |
| (2){3}[3] | 0.3415 ± 0.1606 | 137 | 69 | 7e |
| (2){4}[3][d] | 0.2549 ± 0.1645 | 138 | 69 | 7g |
| (2){5}[3] | 0.3208 ± 0.1905 | 127 | 64 | 7h |
| (2){6}[3] | 0.2887 ± 0.1767 | 137 | 69 | 7i |
| (2){1, 1', 1"}[3] | 0.4380 ± 0.2163 | 393 | 69 | 7c |
| (2){1, 2, 3}[3][c] | 0.3228 ± 0.1713 | 393 | 69 | 7f |

For all three Models, reconstruction error increased slightly when the displacement sampling was reduced to the ROI only (i.e., from Case 1 to Case 2). CaNNCMs trained for Model 1 required the greatest number of AutoP iterations and were unable to capture the peak stiffness of the inclusion. It may be corrected by increasing the number of iterations performed when solving (22). For example, increasing the number of spatial scaling update iterations from 50 to 150 for Model 1, Case 2, the peak stiffness estimated by the CaNNCM is ≈25 kPa (actual is 30 kPa) and the modulus reconstruction error decreases to 0.1291±0.0753. However, preliminary results showed that in the presence of noise, using a large number of iterations could result in overfitting thus magnifying the influence of noise in the Young's modulus reconstruction. It is possible that the addition of a regularization term in (9) could reduce the sensitivity to the number of iterations and noise at the cost of increased computational complexity.

Figure 13:
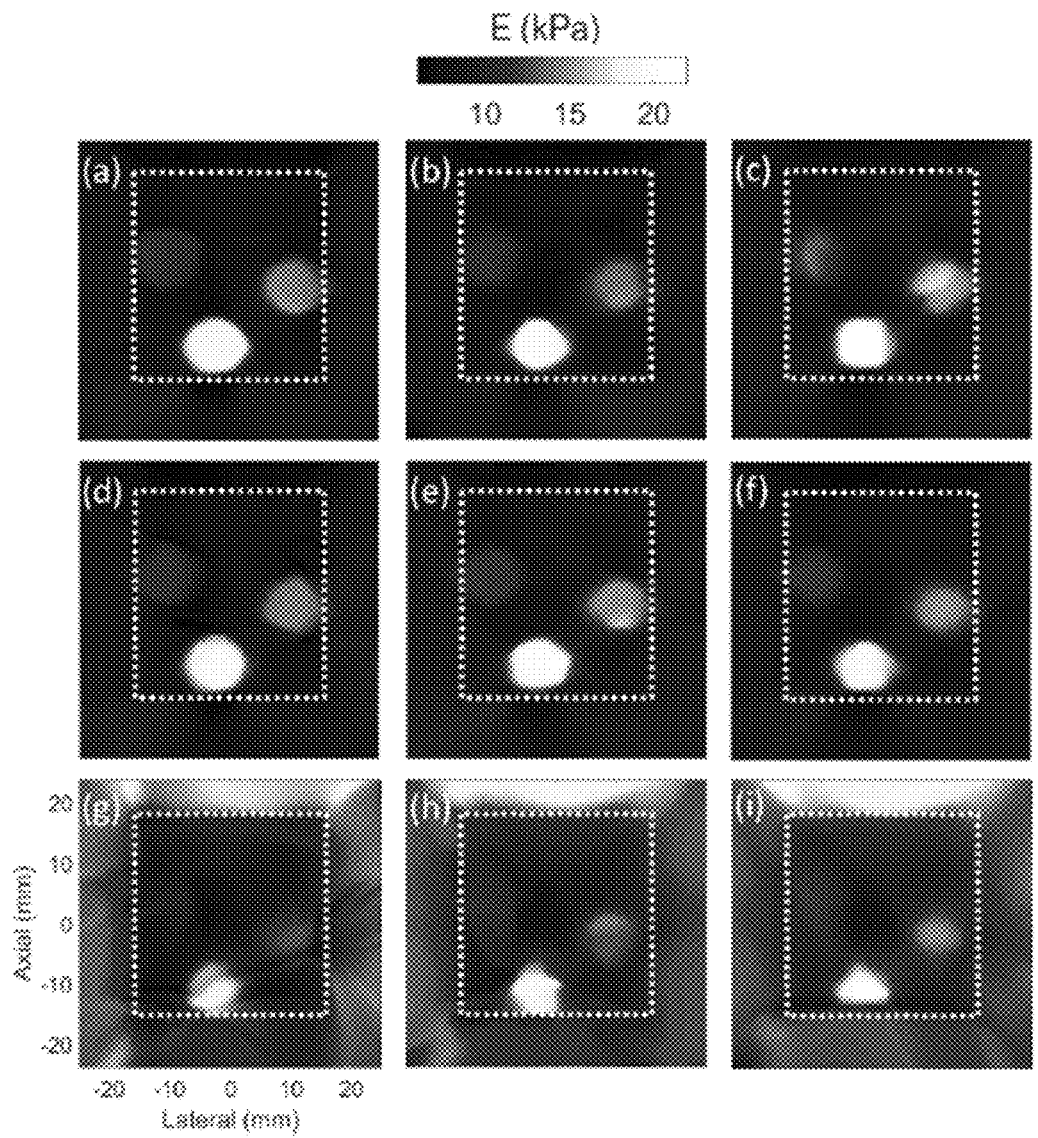
FIG. 13 illustrates Young's modulus images reconstructed by CaNNCMs trained with force-displacement data from Data Sets 1, $1^\dagger$, and $1^{\dagger\wr}$.

FIG. 13 displays the Young's modulus images reconstructed by CaNNCMs trained with force-displacement data from Data Sets 1, $1^{\dagger}$, and $1^{\dagger\dagger}$. Across the columns left to right, the images correspond to Cases 2, 3, and 4, respectively. The smallest error occurs for Set $1^{\dagger\dagger}$, Case 3, albeit the CaNNCM utilized the largest number of AutoP training iterations. For the CaNNCMs trained with Set 1, there is a trade-off between reconstruction error and artifacts in the images. For example, FIG. 13g displays the Young's modulus image with the smallest error for the row, corresponding to Case 2. The error slightly increases for Case 3 (FIG. 13h), but fewer noise artifacts are present. Generally, the trend appears to be that the effect of noise increases as the displacement sampling density increases. The influence of noise can be decreased by reducing sampling density at the cost of resolution and reconstruction accuracy. Note that this applies to the case where only a single data set is used during training. For these reasons, we chose Case 3 sampling for training the remainder of the CaNNCMs with the experimental measurement data.

A stiffening artifact appears between the top of the ROI and phantom surface in the images reconstructed by CaNNCMs trained with experimentally measured force-displacement data (FIGS. 13g-i), but not when trained with simulated RF Data Sets $1^{\dagger}$ or $1^{\dagger\dagger}$ (FIGS. 13a-f). It is likely due to noise occurring in both the force and displacement measurements. Displacements estimated from the simulated RF frames contain noise, but the force measurements are exact. Furthermore, displacements imposed when generating the simulated RF data were obtained from a 2-D FEA whereas the experimental measurements are a 2-D approximation of a 3-D object.

Figure 14:
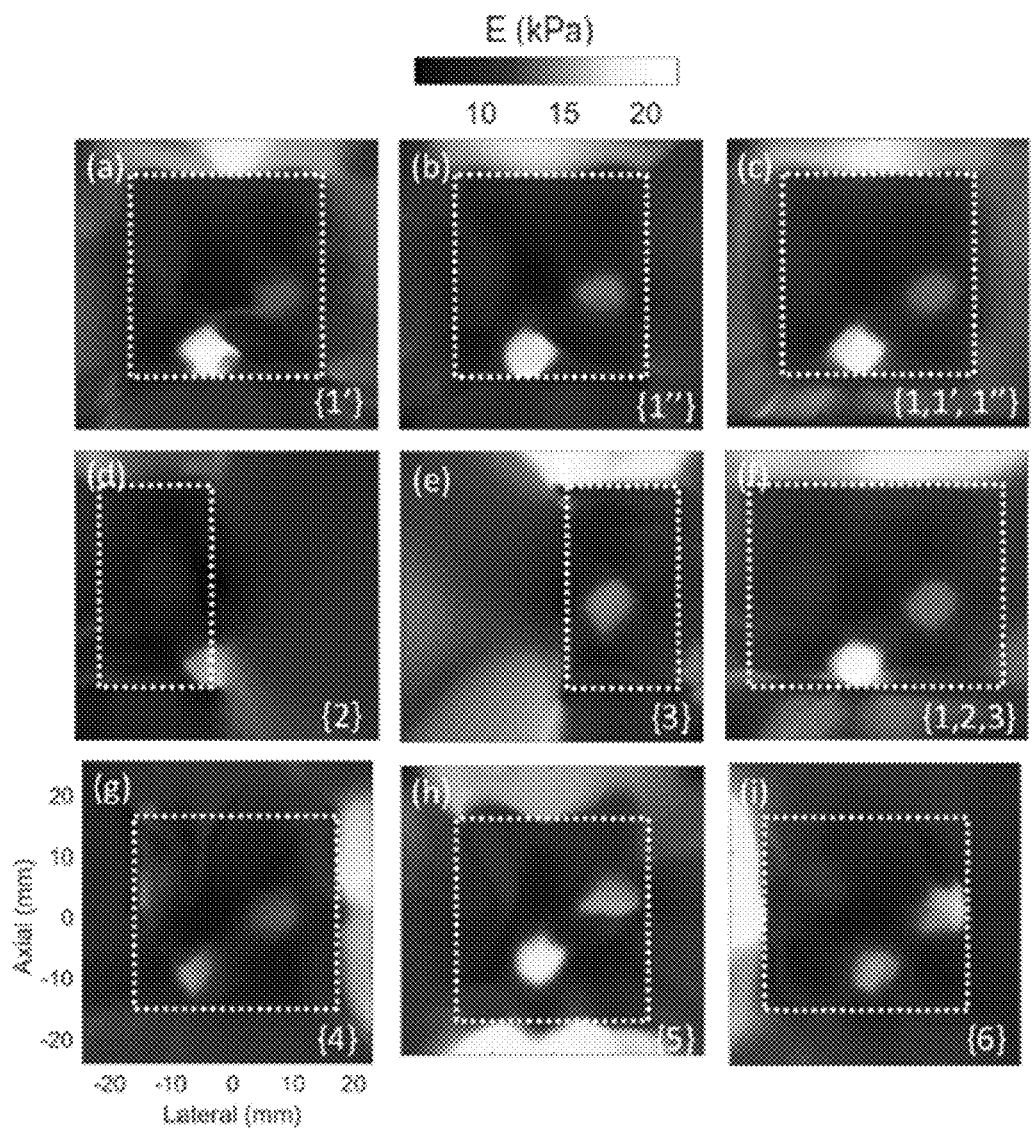
FIG. 14 illustrates Young's modulus images reconstructed by CaNNCMs trained with force-displacement data from experimental measurements.

Young's modulus reconstructions by CaNNCMs trained with experimental measurement data are shown in FIG. 14. Indicated in the bottom-right of each image is/are the Data Set(s) used for training in AutoP. As expected, the Young's modulus estimates are most accurate within the ROI. Reducing the size of the ROI (FIGS. 14d, e) did not inhibit the ability of the CaNNCM to learn the correct material properties. The exception is the inclusion at the bottom of the ROI in FIG. 14d, where the inclusion is only partially within view. Material properties estimated by each CaNNCM are consistent, barring FIGS. 14g and 14i. These correspond to Data Sets 4 and 6, where the phantom was rotated by 90° and 270°, respectively, before data acquisition. Both CaNNCMs learned the correct locations of all three inclusions, but the estimated Young's modulus of the two stiffest inclusions are inaccurate.

It is difficult to identify the source of the error. To determine if the issue was caused by the relative locations of the inclusions within the ROI, a simulated RF data set (using the same methods described previously) was created to mimic Data Set 4. A CaNNCM trained with these data (not shown) was able to accurately estimate modulus values for all three inclusions. Furthermore, if displacement errors computed by (12) and (13) for CaNNCMs corresponding to FIGS. 14a and 14g are compared, there is no significant difference ($C_{max}"=0.0796$, and $C_\mu"=0.0694$ compared to 0.0812 and 0.0692, respectively). Meaning, the CaNNCMs are estimating material properties consistent with the data.

From a qualitative standpoint, including multiple data sets during training (FIGS. 14c, f) improves the appearance of the reconstructed image. The reconstruction error increases when multiple data sets are used. To explore why this occurred, images of the Young's modulus error were generated by computing the difference between the target and reconstructed Young's modulus images. Error maps are displayed in FIG. 15 and the CaNNCMs are indicated in Table II by a superscript. The largest errors occur at the boundaries of the inclusions; most notably, for the stiffest inclusion located at the bottom of the ROI. These maps suggest the largest errors are due to CaNNCMs learning the incorrect geometry. Specifically, the stiffest inclusion appears too small, particularly for CaNNCMs trained with experimental data. Neglecting geometric errors, it was observed that when multiple experimentally measured data sets are used in training (FIG. 15d), the CaNNCM more accurately estimates the Young's modulus of the inclusions. The increased error reported in Table II is mostly attributed to over-estimating the Young's modulus of the background gelatin, by up to 5 kPa in the most extreme cases and mostly toward the boundary of the ROI.

CaNNCMs have been implemented in AutoP to build data-driven constitutive models that learn stress and strain profiles of linear-elastic materials from force-displacement data. Adjusting the NN architecture to learn both material property and geometric information expands the abilities of AutoP by removing any prior assumptions of material property distributions. Additionally, a single CaNNCM can model heterogeneous materials. CaNNCMs are able to model both discrete and continuous material property distributions regardless of the chosen mesh geometry. This is a step toward the use of AutoP in clinical imaging where accurately segmenting images is not always feasible nor possible.

QUSE acquisitions are well suited to data-driven modeling due to the enormous information content in each force-displacement data sample. Quasi-static loading gives the force stimulus time to propagate throughout the entire object before measurements are acquired. Each displacement therefore carries information of not only local material properties, but of the whole contiguous object. AutoP exploits this fact by using FEA to propagate a sparse sampling of force-displacement measurements throughout an entire object model for estimating stresses and strains. Several model-based inverse approaches also rely on FEA to compare computed and measured displacements while estimating the material parameter distribution that best fits the data. However, CaNNCMs trained with AutoP learn stress-strain behavior consistent with the measurement data without prior assumptions of material properties.

A trained CaNNCM can be related back to a known constitutive model to estimate material parameters after learning stress and strain profiles. Young's modulus distribution was estimated via the stiffness matrix to demonstrate a capability of CaNNCMs not possible with model-based methods. When computing $D_{22}$ in (27), there is still no assumption of the constitutive model. The stiffness matrix is effectively recovered from the data.

The additional task of learning the geometric shape of the medium employs a relatively high displacement sampling density. The simulated and experimental measurement data combined with the four displacement sampling cases was intended to provide insight on the trade-off between sampling density, resolution, and modulus estimation accuracy. Results from CaNNCMs trained with noise-free force-displacement data suggest that restricting sampling to the ROI has a slight negative affect on the accuracy of reconstructed Young's modulus images. Data acquired from simulated RF frames and Data Set 1 of the experimental measurements better illustrate the trade-off in FIG. 13. In the presence of noise, dense sampling resulted in more accurate Young's modulus estimates, but artifacts due to noise become more apparent. Conversely, as sampling becomes increasingly sparse, noise artifacts are reduced at the cost of decreased resolution and accuracy of material parameter estimates. Comparing FIGS. 13g-h, the noise artifacts do not obstruct any of the inclusions and are thus not detrimental to the final image. However, it is possible that fine structures could be hidden in more complex media.

Qualitatively, FIGS. 14c and 14f are improvements over training with any one data set: the inclusions are better resolved and fluctuations due to noise are reduced. It is unlikely that increasing the number of passes in AutoP would improve the results considering displacement errors ($C_{max}"$ and $C_\mu"$) computed for the convergence check do not continue to decrease by the end of pass 10. Some of the error can be attributed to the 2-D approximation of 3-D problem, which helps explain why FIGS. 13a-f are much more accurate than FIGS. 13g-i. Extending CaNNCMs to learn volumetric material properties will help to better understand how noise affects the material properties and geometry learned by the networks. The quality of Young's modulus images appears to depend on the coupled effects of spatial sampling and noise, which are not the same as those seen in other applications of QUSE.

AutoP employed 79 minutes to complete on a quad-core CPU operating at 3.4 GHz. As this method is expected to model more complex behaviors in 2-D and 3-D, the run time will tend to increase using the same computing power. Two bottle necks are the use of Abaqus as the FEA solver and training the SN. Abaqus is able to solve the FEAs in seconds but requires much longer to perform a license check and pre-processing step.

AutoP Training Parameters: In the above, each CaNNCM was trained over 10 passes for each data set. A Young's modulus value of 5 kPa and a strain range of ±0.01 was selected for linear-elastic pre-training. $FEA_\sigma$ and $FEA_\varepsilon$ were computed by applying loads to FEM-1.

A four-load training "window" was also incorporated which includes stress-strain data from prior training steps in stages [2]-[4] of the current AutoP iteration. FIG. 9a illustrates the example where training step 3 of pass 3 would also include stresses and strains from training steps 1 and 2 of pass 3 and training steps 3 and 4 of pass 2.

Furthermore, frame invariance was enforced by rotating the stress-strain data 90° and appending the rotated pairs to the original set, effectively doubling the number of stress-strain pairs. Any rotation angle could be used, but 90° was selected because it is easily implemented by swapping the normal components of the data. Building frame invariance into the training data means the material properties learned by the CaNNCM are independent of the chosen coordinate system. With the given training window and enforcement of frame invariance, a total of 19208 stress-strain pairs are used to train the MPN ($N_x \times N_p \times N_\sigma = 19208$ in (19) starting in the second pass.

Spatial scaling values were computed using Algorithm 1 ($N=50$, $N_\sigma=8$ due to frame invariance and training window, spatial scaling update rate $\eta=0.5$). The MPN had two hidden layers of six nodes each, whereas the SN had five hidden layers with ten nodes each. The MPN was trained using the resilient propagation (RPROP) algorithm over 15 epochs. Conversely, the SN training was implemented in Tensor-Flow using the Adam optimizer (with default parameter settings) and a learning rate of 0.03.

Convergence criteria changed as training progressed. Convergence criteria were initialized as (0.65,0.5), using the notation $((C_{max}^n$ and $C_\mu^n)$. These reduced to (0.4,0.3), (0.3, 0.2), and (0.2,0.01) at the beginning of passes 2, 3, and 4, respectively. The last set of criteria were also used in passes 5-10. We chose to set a limit of two AutoP iterations per training step, regardless of whether convergence criteria were satisfied. An upper limit ensures that iterations do not continue indefinitely. We chose a maximum of two based on preliminary results.

Computing Stiffness Matrix From CaNNCM: The "activation" of a node is the weighted sum of the inputs to the node before passing through the activation function. The same analytical function can be used to compute the stiffness matrix for a CaNNCM in response to an input strain with a minor adjustment:

$$D_{ij}(x) = \frac{\partial \sigma_i(x)}{\partial e_j(x)} \frac{S_i^\sigma}{S_x^{\varepsilon i}} = \frac{S_i^\sigma}{S_x^{\varepsilon j}} \hat{D}_{ij}(x) \quad (29)$$

where $$\hat{D}_{ij} = (1 - \tanh(f_i)^2) \sum_{c=1}^{N_{h_2}} \left[ w_{ic}(1 - \tanh(f_c)^2) \times \sum_{b=1}^{N_{h_1}} \left\{ w_{cb}(1 - \tanh(f_b)^2) \sum_{a=1}^{N_i} (w_{ba}(1 - \tanh(\varepsilon_j)^2)) \right\} \right]. \quad (30)$$

In (30), the values $f_i$, $f_c$, and $f_b$ are the activations of nodes in the output layer, second hidden layer, and first hidden layer, respectively. $N_{h_2}$ is the number of nodes in the second hidden layer, $N_{h_1}$ is the number of nodes in the first hidden layer, and Ni specifies the number of nodes in the input layer. Weights from node p in layer N−1 to node q in layer N are denoted as $\omega_{qp}$.

The preceding results demonstrate the ability of CaNNCMs to learn both material property and spatial information in 2-D. However, in vivo elasticity imaging is inherently a 3-D problem. Furthermore, the mechanical properties of soft tissues are very complex and will likely require force-displacement measurements to be acquired by an US probe compressing the tissue surface from many locations and angles. Effective use of such measurement data requires 3-D capabilities.

Figure 16A:
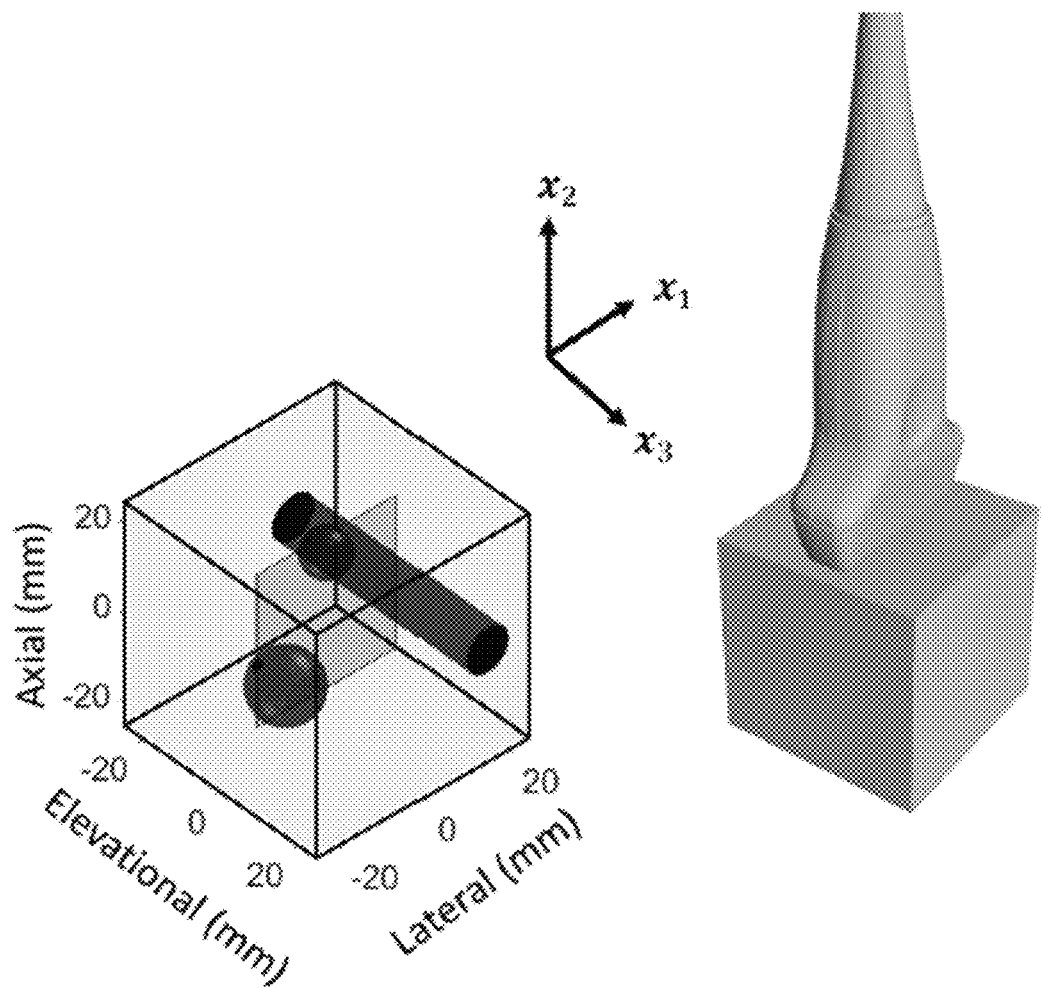
FIG. 16A illustrates an exemplary phantom with inclusions.
Figure 16B:
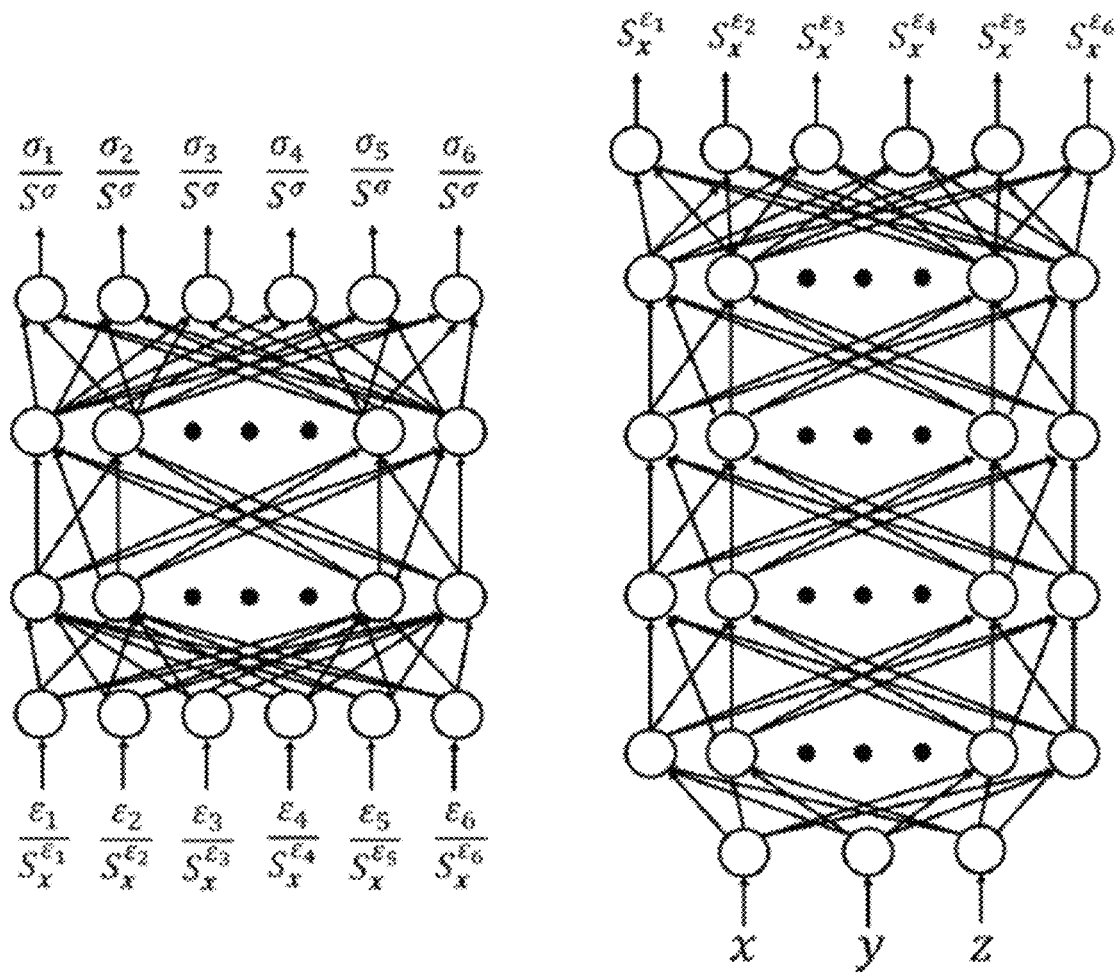
FIG. 16B illustrates an alternate embodiment of a CaNNCMs for use with the system of FIG. 1 in accordance with one or more aspects of the described technology; and, FIG. 17 illustrates a comparison of target and estimated 3-D Young's modulus distributions for one, three and seven independent scan planes in accordance with one or more aspects of the described technology.

FIG. 16a illustrates an architecture of a 3-D CaNNCM. Compared to its 2-D counterpart, it includes an increase in the number of inputs and outputs of both the MPN and SN. The 3-D imaging capabilities are demonstrated by acquiring force-displacement measurements on the gelatin phantom shown in the left of FIG. 16b. It includes three stiff inclusions—two spherical and one cylindrical—embedded in a soft background. The image on the right side of FIG. 16b illustrates one possible loading orientation of the US probe. In this example, a total of seven force-displacement measurements were acquired by translating the US probe along the elevational ($x_3$) axis before each set of compressions.

The internal displacements estimated from RF echo frames contain an immense amount of information pertaining to the spatial distribution of material properties. Conversely, the surface force measurements are integrated point loads over a portion of the boundary. As a consequence, stresses computed in $FEA_\sigma$ are physically consistent on average over the domain of the material but contain limited spatial information. CaNNCMs trained in AutoP can more accurately learn material properties by introducing a new regularization term, denoted σ-matching. First, the difference between stresses of $\sigma_l^n(x_i)$ computed in FEA, and stresses of $\overline{\sigma}_l^n(x_i)$ computed in $FEA_\varepsilon$ are calculated, $$\Delta \sigma_l^n(x_i) = |\sigma_l^n(x_i) - \overline{\sigma}_l^n(x_i)| \cdot \text{sign}(\sigma_l^n(x_i)). \quad (31)$$

The stress difference is then adjusted to have zero mean in each component:

$$\mu_l^n = \frac{1}{N_x} \sum_{i=1}^{N_x} \Delta \sigma_l^n(x_i), \quad (32)$$

$$\mathcal{R}(\Delta \sigma_l^n(x_i)) = \Delta \sigma_l^n(x_i) - \mu_l^n. \quad (33)$$

The regularization term $\mathcal{R}(\Delta \sigma_l^n(x_i))$ is weighted by $\beta_\sigma$ and added to the loss function when computing spatial scaling values, $$S_{x_i}^s = \underset{\hat{S}_{x_i}^\varepsilon \in R}{\text{argmin}} \frac{1}{2} \sum_{n=1}^{N_p} \sum_{l=1}^{N_\sigma} (\sigma_l^n(x_i) - \hat{\sigma}_l^n(\varepsilon_l^n(x_i); R_{\theta_m}^{j+1}, \hat{S}_{x_i}^\varepsilon) + \beta_\sigma \mathcal{R}(\Delta \sigma_l^n(x_i))^2. \quad (34)$$

σ-matching is uniquely suited for AutoP because of the relationship between force-displacement boundary conditions and stress-strain fields. The tight coupling between CaNNCMs and FEA ensure the trained soft-computational models are consistent with physical principles. By adding σ-matching, an additional physical constraint is imposed to stabilize the solution and lead to more accurate material property estimates.

Figure 17:
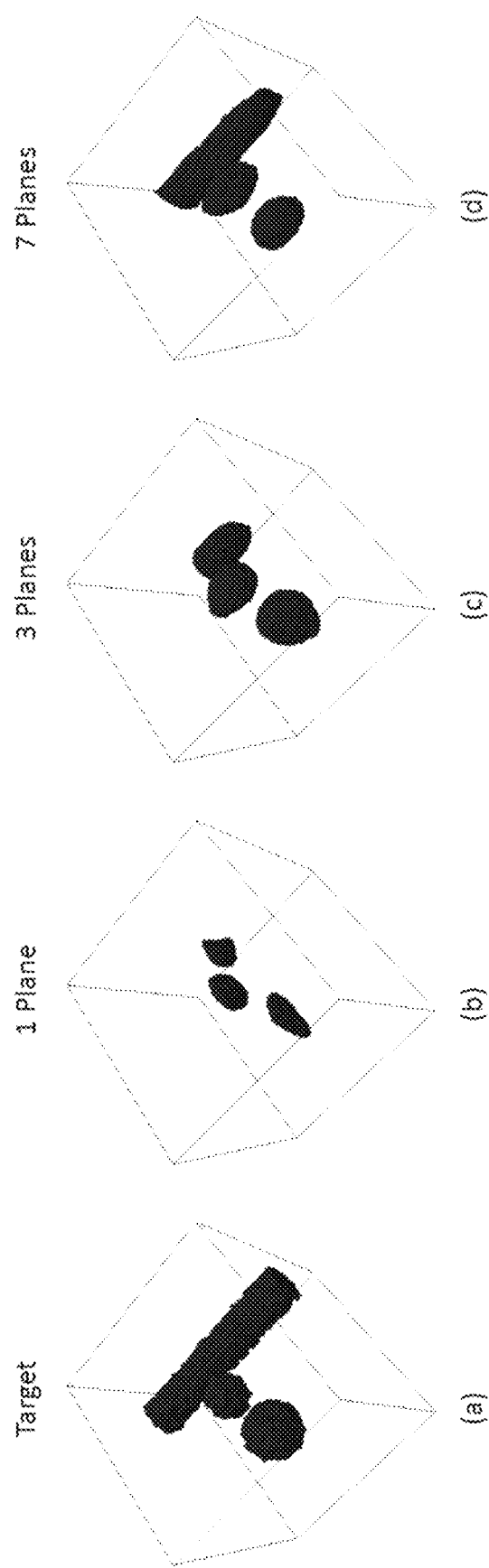

An example of the 3-D material properties reconstructed by CaNNCMs trained in AutoP are displayed in FIG. 17. The ground truth geometry of the inclusions are shown in FIG. 17, (a). By including internal displacements from 1, 3, or 7 parallel scan planes (FIG. 17, (b)-(d)) and imposing o-matching during training, CaNNCMs better learn material properties through a volume.

Having thus described preferred embodiments of the technology, advantages can be appreciated. Variations from the described embodiments exist without departing from the scope of the claimed technology. Informational models trained using AutoP have an ability to learn mechanical behavior from quasi-static measurements of surface forces and sparse displacement information. This approach has advantages when the mechanical properties of the medium are not well characterized, which is the situation in medical elasticity imaging. The conventional parametric inverse problem approach involving numerous assumptions is traded for a nonparametric machine-learning technique. This technique learns to model stress and strain fields from which imaging parameters are found. The ability of informational models to accurately predict mechanical behavior is limited by the type and amount of force-displacement information provided. Model accuracy can be improved by adding data from different spatial views and distributing measurement data for FEA training and convergence testing. Informational models have the ability to accumulate knowledge, which minimizes training time. Although particular embodiments and examples have been disclosed herein in detail, this has been done for purposes of illustration only, and is not intended to be limiting with respect to the scope of the claims, which follow. In particular, it is contemplated by the inventors that various substitutions, alterations, and modifications may be made without departing from the spirit and scope of the technology as defined by the claims. Other aspects, advantages, and modifications are considered to be within the scope of the following claims. The claims presented are representative of the technology disclosed herein. Other, unclaimed technology is also contemplated. The inventors reserve the right to pursue such technology in later claims.

Insofar as embodiments of the technology described above are implemented, at least in part, using a computer system, it will be appreciated that a computer program for implementing at least part of the described methods and/or the described systems is envisaged as an aspect of the technology. The computer system may be any suitable apparatus, system or device, electronic, optical, or a combination thereof. For example, the computer system may be a programmable data processing apparatus, a computer, a Digital Signal Processor, an optical computer or a microprocessor. The computer program may be embodied as source code and undergo compilation for implementation on a computer, or may be embodied as object code, for example.

It is accordingly intended that all matter contained in the above description or shown in the accompanying drawings be interpreted as illustrative rather than in a limiting sense. It is also to be understood that the following claims are intended to cover all of the generic and specific features of the technology as described herein, and all statements of the scope of the technology which, as a matter of language, might be said to fall there between.

Having described the technology, what is claimed as new and secured by Letters Patent is:

The invention claimed is:

1. A computer-implemented method for improved estimation of stress and strain distributions in biological tissue without requiring assumptions about underlying constitutive models, the method comprising:

applying with a probe, a plurality of forces to the tissue;

obtaining and recording a series of displacement measurements respectively over a period of time resulting from the plurality of forces, wherein the displacement measurements are recorded from a plurality of locations on the tissue; wherein each of the plurality of locations can be respectively identified by a set of spatial coordinates;

providing the force, and the displacement measurements and at least one set of special coordinates to a processor-based device;

using the processor-based device to generate, based at least in part on the force, and the displacement measurements and the spatial coordinates, the estimates of stress and strain distributions within the biological tissue; and applying the set of spatial coordinates to a Cartesian neural network constitutive model (CaNNCM).

2. The method according to claim 1 wherein the plurality of forces are quasi-static forces.

3. The method according to claim 1 further including the processor-based device estimating a plurality of parameters from at least one of the constitutive models based on a plurality of the forces and the displacement measurements.

4. The method according to claim 3 wherein the processor-based device implements an Autoprogressive ("AutoP") algorithm to estimate the plurality of parameters.

5. The method according to claim 4 further comprising the processor-based device applying a scaling factor to the force and displacement measurements, comparing the scaled force and displacement measurements to a predetermined range and increasing the scaling factor when the scaled force and displacement measurements fall outside the predetermined range.

6. The method according to claim 4 wherein the AutoP algorithm employs a plurality of finite element analyses (FEAs) to respectively relate the forces and the stresses and the displacement and the strain at at least two sets of the spatial coordinates.

7. The method according to claim 6 wherein the AutoP Algorithm relates the FEAs through the CaNNCM.

8. The method according to claim 7 wherein the CaNNCM includes a plurality of CaNNCMs.

9. The method according to claim 1 further including the processor-based device learning a spatial information by multiplying a strain vector by a stiffness matrix and computing a stress corresponding to the spatial information for at least two of the sets of spatial coordinates.

10. The method according to claim 1 further including the processor-based device learning a spatial information by multiplying a strain vector by a spatially varying value and computing a stress corresponding to the spatial information for at least two of the sets of spatial coordinates.

11. The method according to claim 1 further including generating a radio frequency (RF) signal from an ultrasound transducer and transmitting the RF signal into the tissue.

12. The method according to claim 1 further including positioning the probe in relation to the tissue with a positioning system.

13. A computer-implemented method for improved estimation of stress and strain distributions and geometric properties in biological tissue without requiring assumptions about underlying constitutive models, the method comprising:

positioning a probe based on a set of spatial coordinates in relation to the tissue, with a positioning system;

applying with the probe, a plurality of external forces to the tissue and storing at least one of the applied external forces;

recording a series of internal and external displacement measurements respectively, over a period of time, resulting from the plurality of forces, wherein the measurements are recorded from a plurality of locations on the tissue;

providing the force, and the displacement measurements to a processor-based device;

the processor-based device receiving the force, and the displacement measurements and developing an informational model of mechanical and geometric properties of the tissue using an Autoprogressive ("AutoP") Algorithm;

using the processor-based device to generate, based at least in part on the force and displacement measurements, an estimate of stress and strain distributions and geometric properties within the biological tissue; and applying the set of spatial coordinates to a cartesian neural network constitutive model (CaNNCM).

14. The method according to claim 13 further including the processor-based device estimating a plurality of parameters from at least one of the underlying constitutive models based on a plurality of the forces and the displacement measurements.

15. The method according to claim 14 wherein the processor-based device implements the Autoprogressive ("AutoP") algorithm to estimate the plurality of parameters.

16. The method according to claim 15 further comprising the processor-based device incorporating a plurality of the sets of spatial coordinates with the force and displacement measurements.

17. The method according to claim 15 wherein the AutoP algorithm employs a plurality of finite element analyses (FEAs) to respectively relate the forces and the stresses and the displacement and the strain at a plurality of the sets of spatial coordinates.

18. The method according to claim 17 wherein the AutoP Algorithm relates the FEAs through the CaNNCM.

19. The method according to claim 18 wherein at least one CaNNCM includes a plurality of CaNNCMs.

20. The method according to claim 13 further including the processor-based device modifying the estimate of the geometric properties of the tissue by relating the set of spatial coordinates with the estimated stress and strain distributions.

* * * * *